United States Patent
Desecki

(10) Patent No.: US 7,753,338 B2
(45) Date of Patent: Jul. 13, 2010

(54) LUER ACTIVATED DEVICE WITH MINIMAL FLUID DISPLACEMENT

(75) Inventor: Vincent C. Desecki, Spring Grove, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 259 days.

(21) Appl. No.: 11/876,630

(22) Filed: Oct. 22, 2007

(65) Prior Publication Data

US 2008/0093571 A1  Apr. 24, 2008

Related U.S. Application Data

(60) Provisional application No. 60/862,502, filed on Oct. 23, 2006.

(51) Int. Cl.
*F16K 51/00* (2006.01)

(52) U.S. Cl. .......... 251/149.8; 251/149.6; 604/249; 604/905

(58) Field of Classification Search .......... 251/149.1, 251/149.3, 149.4, 149.6, 149.8; 604/246, 604/249, 256, 95.04, 95.05, 523, 528, 533, 604/534, 535, 537, 538, 539, 905; 600/4, 600/434, 435, 585

See application file for complete search history.

(56) References Cited

U.S. PATENT DOCUMENTS

| 4,176,588 A | 12/1979 | Baron |
|---|---|---|
| 4,334,551 A | 6/1982 | Pfister |
| 4,413,462 A | 11/1983 | Rose |
| 4,475,548 A | 10/1984 | Muto |
| 4,691,929 A | 9/1987 | Neumaier et al. |
| 4,928,212 A | 5/1990 | Benavides |
| 4,943,896 A | 7/1990 | Johnson |
| 4,946,445 A | 8/1990 | Lynn |
| 4,964,855 A | 10/1990 | Todd et al. |
| 4,973,443 A | 11/1990 | Larson et al. |
| 4,998,713 A | 3/1991 | Vaillancourt |
| 4,998,927 A | 3/1991 | Vaillancourt |
| 5,009,490 A | 4/1991 | Kouno et al. |
| 5,019,325 A | 5/1991 | Larson et al. |
| 5,046,456 A | 9/1991 | Heyman et al. |
| D321,250 S | 10/1991 | Jepson et al. |
| D321,251 S | 10/1991 | Jepson et al. |
| 5,064,416 A | 11/1991 | Newgard et al. |
| 5,065,783 A | 11/1991 | Ogle, II |
| 5,100,394 A | 3/1992 | Dudar et al. |
| 5,114,408 A | 5/1992 | Fleischhaker et al. |
| 5,122,123 A | 6/1992 | Vaillancourt |

(Continued)

FOREIGN PATENT DOCUMENTS

CA  1105959  7/1981

(Continued)

*Primary Examiner*—John K Fristoe, Jr.
(74) *Attorney, Agent, or Firm*—K&L Gates LLP

(57) ABSTRACT

A luer activated device includes an inlet adapted to receive a male luer, an outlet associable with a fluid flow system, and a flow path defined therebetween. The inlet receives a resealable valve element having an aperture adapted to receive the male luer. The valve element is adapted such that a male luer inserted into the aperture will open fluid flow through the inlet without causing a substantial change in fluid displacement.

21 Claims, 9 Drawing Sheets

U.S. PATENT DOCUMENTS

| | | | |
|---|---|---|---|
| 5,135,489 A | 8/1992 | Jepson et al. |
| 5,154,703 A | 10/1992 | Bonaldo |
| 5,158,554 A | 10/1992 | Jepson et al. |
| 5,171,234 A | 12/1992 | Jepson et al. |
| 5,188,620 A | 2/1993 | Jepson et al. |
| 5,199,947 A | 4/1993 | Lopez et al. |
| 5,201,717 A | 4/1993 | Wyatt et al. |
| 5,203,775 A | 4/1993 | Frank et al. |
| 5,211,638 A | 5/1993 | Dudar et al. |
| 5,242,393 A | 9/1993 | Brimhall et al. |
| 5,242,425 A | 9/1993 | White et al. |
| 5,242,432 A | 9/1993 | DeFrank |
| 5,251,873 A | 10/1993 | Atkinson et al. |
| 5,256,155 A | 10/1993 | Yerlikaya et al. |
| 5,269,763 A | 12/1993 | Boehmer et al. |
| 5,269,771 A | 12/1993 | Thomas et al. |
| 5,280,876 A | 1/1994 | Atkins |
| 5,290,254 A | 3/1994 | Vaillancourt |
| 5,295,657 A | 3/1994 | Atkinson |
| 5,295,658 A | 3/1994 | Atkinson et al. |
| 5,312,377 A | 5/1994 | Dalton |
| 5,323,264 A | 6/1994 | Kato |
| 5,324,270 A | 6/1994 | Kayan et al. |
| 5,344,414 A | 9/1994 | Lopez et al. |
| 5,360,413 A | 11/1994 | Leason et al. |
| 5,401,245 A | 3/1995 | Haining |
| 5,402,982 A | 4/1995 | Atkinson et al. |
| 5,411,499 A | 5/1995 | Dudar et al. |
| 5,417,673 A | 5/1995 | Gordon |
| 5,470,319 A | 11/1995 | Mayer |
| 5,487,731 A | 1/1996 | Denton |
| 5,492,147 A * | 2/1996 | Challender et al. ..... 137/614.05 |
| 5,514,109 A | 5/1996 | Mollenauer et al. |
| 5,533,708 A | 7/1996 | Atkinson et al. |
| 5,540,661 A | 7/1996 | Tomisaka et al. |
| 5,549,566 A | 8/1996 | Elias et al. |
| 5,549,651 A | 8/1996 | Lynn |
| 5,556,388 A | 9/1996 | Johlin, Jr. |
| 5,578,059 A | 11/1996 | Patzer |
| 5,602,016 A | 2/1997 | Isogai et al. |
| 5,609,584 A | 3/1997 | Gettig et al. |
| 5,616,129 A | 4/1997 | Mayer |
| 5,616,130 A | 4/1997 | Mayer |
| 5,676,346 A | 10/1997 | Leinsing |
| 5,677,141 A | 10/1997 | Isogai et al. |
| 5,685,866 A | 11/1997 | Lopez |
| 5,690,612 A | 11/1997 | Lopez et al. |
| 5,695,466 A | 12/1997 | Lopez et al. |
| 5,699,821 A | 12/1997 | Paradis |
| 5,700,248 A | 12/1997 | Lopez |
| 5,730,418 A | 3/1998 | Feith et al. |
| 5,738,663 A | 4/1998 | Lopez |
| 5,773,272 A | 6/1998 | Isogai et al. |
| RE35,841 E | 7/1998 | Frank et al. |
| 5,788,675 A | 8/1998 | Mayer |
| 5,797,897 A | 8/1998 | Jepson et al. |
| 5,820,601 A | 10/1998 | Mayer |
| 5,836,923 A | 11/1998 | Mayer |
| 5,865,807 A | 2/1999 | Blake, III |
| 5,873,862 A | 2/1999 | Lopez |
| 5,901,942 A | 5/1999 | Lopez |
| 5,928,204 A | 7/1999 | Lopez |
| 5,957,898 A | 9/1999 | Jepson et al. |
| 5,967,490 A | 10/1999 | Pike |
| 5,971,965 A | 10/1999 | Mayer |
| RE36,587 E | 2/2000 | Tanaka et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| RE36,661 E | 4/2000 | Tanaka et al. |
| 6,048,335 A | 4/2000 | Mayer |
| 6,089,541 A | 7/2000 | Weinheimer et al. |
| 6,113,068 A * | 9/2000 | Ryan ....................... 251/149.4 |
| 6,132,403 A | 10/2000 | Lopez |
| 6,132,404 A | 10/2000 | Lopez |
| 6,146,396 A | 11/2000 | Konya et al. |
| 6,152,900 A | 11/2000 | Mayer |
| 6,162,251 A | 12/2000 | Kredovski |
| 6,171,287 B1 | 1/2001 | Lynn et al. |
| 6,177,037 B1 | 1/2001 | Mayer |
| 6,183,448 B1 | 2/2001 | Mayer |
| 6,187,476 B1 | 2/2001 | Pyun et al. |
| 6,210,624 B1 | 4/2001 | Mayer |
| 6,228,069 B1 | 5/2001 | Barth et al. |
| 6,245,048 B1 | 6/2001 | Fangrow, Jr. et al. |
| 6,261,268 B1 | 7/2001 | Mayer |
| 6,261,282 B1 | 7/2001 | Jepson et al. |
| 6,290,206 B1 | 9/2001 | Doyle |
| 6,299,132 B1 | 10/2001 | Weinheimer et al. |
| 6,325,782 B1 | 12/2001 | Lopez |
| 6,341,802 B1 | 1/2002 | Matkovich |
| 6,344,033 B1 | 2/2002 | Jepson et al. |
| 6,355,023 B1 | 3/2002 | Roth et al. |
| 6,364,869 B1 | 4/2002 | Bonaldo |
| 6,374,876 B2 | 4/2002 | Bynum |
| 6,383,168 B1 | 5/2002 | Landau et al. |
| 6,390,120 B1 | 5/2002 | Guala |
| 6,390,130 B1 | 5/2002 | Guala |
| 6,394,983 B1 | 5/2002 | Mayoral et al. |
| 6,394,992 B1 | 5/2002 | Sjoholm |
| 6,402,723 B1 | 6/2002 | Lampropoulos |
| 6,408,897 B1 | 6/2002 | Laurent et al. |
| 6,409,707 B1 | 6/2002 | Guala |
| 6,409,708 B1 | 6/2002 | Wessman |
| 6,423,053 B1 | 7/2002 | Lee |
| 6,428,520 B1 | 8/2002 | Lopez et al. |
| 6,440,107 B1 | 8/2002 | Trombley, III et al. |
| 6,467,732 B2 | 10/2002 | Tsukahara |
| 6,481,756 B1 | 11/2002 | Field et al. |
| 6,482,188 B1 | 11/2002 | Rogers et al. |
| 6,485,472 B1 | 11/2002 | Richmond |
| 6,486,630 B2 | 11/2002 | Takagi |
| 6,491,668 B1 | 12/2002 | Paradis |
| 6,508,807 B1 | 1/2003 | Peters |
| 6,520,932 B2 | 2/2003 | Taylor |
| 6,536,805 B2 | 3/2003 | Matkovich |
| 6,537,258 B1 | 3/2003 | Guala |
| 6,539,248 B1 | 3/2003 | Moroski |
| 6,541,802 B2 | 4/2003 | Doyle |
| 6,543,745 B1 | 4/2003 | Enerson |
| 6,544,236 B1 | 4/2003 | Cragg et al. |
| 6,569,118 B2 | 5/2003 | Johnson et al. |
| 6,569,125 B2 | 5/2003 | Jepson et al. |
| RE38,145 E | 6/2003 | Lynn |
| 6,572,590 B1 | 6/2003 | Stevens et al. |
| 6,572,591 B2 | 6/2003 | Mayer |
| 6,572,592 B1 | 6/2003 | Lopez |
| 6,581,906 B2 | 6/2003 | Pott et al. |
| 6,585,229 B2 | 7/2003 | Cote, Sr. et al. |
| 6,595,954 B1 | 7/2003 | Luther et al. |
| 6,595,964 B2 | 7/2003 | Finley et al. |
| 6,599,273 B1 | 7/2003 | Lopez |
| 6,605,076 B1 | 8/2003 | Jepson et al. |
| 6,609,696 B2 | 8/2003 | Enerson |
| 6,620,119 B1 | 9/2003 | Utterberg et al. |
| 6,626,418 B2 | 9/2003 | Kiehne |
| 6,634,033 B2 | 10/2003 | Mizuno et al. |
| 6,635,044 B2 | 10/2003 | Lopez |
| 6,638,244 B1 | 10/2003 | Reynolds |
| 6,638,258 B2 | 10/2003 | Schwartz et al. |
| 6,651,956 B2 | 11/2003 | Miller |
| 6,655,655 B1 | 12/2003 | Matkovich et al. |
| 6,666,839 B2 | 12/2003 | Utterberg et al. |

| Patent/Pub No. | Date | Name |
|---|---|---|
| 6,669,673 B2 | 12/2003 | Lopez |
| 6,669,681 B2 | 12/2003 | Jepson et al. |
| 6,673,059 B2 | 1/2004 | Guala |
| 6,679,529 B2 | 1/2004 | Johnson et al. |
| 6,681,810 B2 | 1/2004 | Weston |
| 6,682,509 B2 | 1/2004 | Lopez |
| 6,695,817 B1 | 2/2004 | Fangrow, Jr. |
| 6,699,222 B1 | 3/2004 | Jones et al. |
| 6,706,022 B1 | 3/2004 | Leinsing et al. |
| 6,716,187 B1 | 4/2004 | Jorgensen et al. |
| 6,716,189 B1 | 4/2004 | Jarvik et al. |
| 6,722,705 B2 | 4/2004 | Korkor |
| 6,723,074 B1 | 4/2004 | Halseth |
| 6,726,651 B1 | 4/2004 | Robinson et al. |
| 6,726,672 B1 | 4/2004 | Hanly et al. |
| 6,730,883 B2 | 5/2004 | Brown et al. |
| 6,745,998 B2 | 6/2004 | Doyle |
| 6,746,438 B1 | 6/2004 | Arnissolle |
| 6,755,391 B2 | 6/2004 | Newton et al. |
| 6,758,833 B2 | 7/2004 | Lopez |
| 6,770,051 B2 | 8/2004 | Hughes et al. |
| 6,802,490 B2 | 10/2004 | Leinsing et al. |
| 6,802,836 B2 | 10/2004 | Bouphavichith et al. |
| 6,808,161 B1 | 10/2004 | Hishikawa |
| 6,808,509 B1 | 10/2004 | Davey |
| 6,811,139 B2 | 11/2004 | Hishikawa |
| 6,814,726 B1 | 11/2004 | Lauer |
| 6,827,709 B2 | 12/2004 | Fujii |
| 6,827,710 B1 | 12/2004 | Mooney et al. |
| 6,834,842 B2 | 12/2004 | Houde |
| 6,840,501 B2 | 1/2005 | Doyle |
| 6,843,513 B2 | 1/2005 | Guala |
| 6,866,656 B2 | 3/2005 | Tingey et al. |
| 6,869,426 B2 | 3/2005 | Ganem |
| 6,871,087 B1 | 3/2005 | Hughes et al. |
| 6,874,522 B2 | 4/2005 | Anderson et al. |
| 6,878,905 B2 | 4/2005 | Brown et al. |
| 6,880,801 B2 | 4/2005 | Matkovich et al. |
| 6,883,778 B1 | 4/2005 | Newton et al. |
| 6,893,056 B2 | 5/2005 | Guala |
| 6,902,207 B2 | 6/2005 | Lickliter |
| 6,908,459 B2 | 6/2005 | Harding et al. |
| 6,911,025 B2 | 6/2005 | Miyahara |
| 6,916,309 B2 | 7/2005 | Fangrow, Jr. |
| 6,918,500 B2 | 7/2005 | Okiyama |
| 6,932,795 B2 | 8/2005 | Lopez et al. |
| 6,953,450 B2 | 10/2005 | Baldwin et al. |
| 6,955,669 B2 | 10/2005 | Curutcharry |
| 6,960,198 B2 | 11/2005 | Sarmiento |
| 6,964,406 B2 | 11/2005 | Doyle |
| 6,969,381 B2 | 11/2005 | Voorhees |
| 6,972,001 B2 | 12/2005 | Emig et al. |
| 6,974,446 B2 | 12/2005 | Hommann et al. |
| 6,994,315 B2 * | 2/2006 | Ryan et al. ............ 251/149.6 |
| 7,004,934 B2 | 2/2006 | Vaillancourt |
| 7,008,406 B2 | 3/2006 | Mayer |
| 7,014,169 B2 | 3/2006 | Newton et al. |
| 7,025,744 B2 | 4/2006 | Utterberg et al. |
| 7,033,339 B1 | 4/2006 | Lynn |
| 7,037,302 B2 | 5/2006 | Vaillancourt et al. |
| 7,041,087 B2 | 5/2006 | Henderson et al. |
| 7,044,441 B2 | 5/2006 | Doyle |
| 7,044,937 B1 | 5/2006 | Kirwan et al. |
| 7,081,600 B2 | 7/2006 | Brown et al. |
| 7,083,605 B2 | 8/2006 | Miyahara |
| 7,090,191 B2 | 8/2006 | Matkovich et al. |
| 7,097,209 B2 | 8/2006 | Sparrman et al. |
| 7,100,891 B2 | 9/2006 | Doyle |
| 7,104,520 B2 | 9/2006 | Leinsing et al. |
| RE39,334 E | 10/2006 | Lynn |
| 7,114,701 B2 | 10/2006 | Peppel |
| 7,118,560 B2 | 10/2006 | Bonaldo |
| 7,128,348 B2 | 10/2006 | Kawamura et al. |
| 7,137,974 B2 | 11/2006 | Almasian et al. |
| 7,140,592 B2 | 11/2006 | Phillips |
| 7,153,296 B2 | 12/2006 | Mitchell |
| 7,156,826 B2 | 1/2007 | Ishii et al. |
| 7,160,272 B1 | 1/2007 | Eyal et al. |
| RE39,499 E | 2/2007 | Racz |
| 7,172,572 B2 | 2/2007 | Diamond et al. |
| 7,174,923 B2 | 2/2007 | Schorn et al. |
| 7,175,615 B2 | 2/2007 | Hanly et al. |
| 7,182,313 B2 | 2/2007 | Doyle |
| 7,184,825 B2 | 2/2007 | Leinsing et al. |
| 2001/0045539 A1 | 11/2001 | Doyle |
| 2001/0049508 A1 | 12/2001 | Fangrow et al. |
| 2001/0051791 A1 | 12/2001 | Azzolini |
| 2001/0051793 A1 | 12/2001 | Weston |
| 2002/0007157 A1 | 1/2002 | Azzolini |
| 2002/0024036 A1 | 2/2002 | Rohrbough et al. |
| 2002/0032433 A1 | 3/2002 | Lopez |
| 2002/0038114 A1 | 3/2002 | Segura |
| 2002/0062106 A1 | 5/2002 | Chu et al. |
| 2002/0082586 A1 | 6/2002 | Finley et al. |
| 2002/0099360 A1 | 7/2002 | Bierman |
| 2002/0108614 A1 | 8/2002 | Schultz |
| 2002/0115981 A1 | 8/2002 | Wessman |
| 2002/0115984 A1 | 8/2002 | Guala |
| 2002/0117645 A1 | 8/2002 | Kiehne |
| 2002/0128595 A1 | 9/2002 | Weston et al. |
| 2002/0128607 A1 | 9/2002 | Haury et al. |
| 2002/0133124 A1 | 9/2002 | Leinsing et al. |
| 2002/0138047 A1 | 9/2002 | Lopez |
| 2002/0143300 A1 | 10/2002 | Trombley et al. |
| 2002/0143301 A1 | 10/2002 | Lopez |
| 2002/0147429 A1 | 10/2002 | Cowan et al. |
| 2002/0147431 A1 | 10/2002 | Lopez et al. |
| 2002/0153503 A1 | 10/2002 | Newton et al. |
| 2002/0156431 A1 | 10/2002 | Feith et al. |
| 2002/0161334 A1 | 10/2002 | Castellano et al. |
| 2002/0193752 A1 | 12/2002 | Lynn |
| 2003/0028156 A1 | 2/2003 | Juliar |
| 2003/0032940 A1 | 2/2003 | Doyle |
| 2003/0036735 A1 | 2/2003 | Jepson et al. |
| 2003/0050610 A1 | 3/2003 | Newton et al. |
| 2003/0060779 A1 | 3/2003 | Richmond |
| 2003/0060804 A1 | 3/2003 | Vaillancourt |
| 2003/0066978 A1 | 4/2003 | Enerson |
| 2003/0066980 A1 | 4/2003 | Hishikawa |
| 2003/0085372 A1 | 5/2003 | Newton |
| 2003/0093061 A1 | 5/2003 | Ganem |
| 2003/0098430 A1 | 5/2003 | Leinsing et al. |
| 2003/0105452 A1 | 6/2003 | Mayer |
| 2003/0109853 A1 | 6/2003 | Harding et al. |
| 2003/0120221 A1 | 6/2003 | Vaillancourt |
| 2003/0127620 A1 | 7/2003 | Houde |
| 2003/0141477 A1 | 7/2003 | Miller |
| 2003/0144626 A1 | 7/2003 | Hanson et al. |
| 2003/0144647 A1 | 7/2003 | Miyahara |
| 2003/0181850 A1 | 9/2003 | Diamond et al. |
| 2003/0181854 A1 | 9/2003 | Sauvageau |
| 2003/0183795 A1 | 10/2003 | Doyle |
| 2003/0195478 A1 | 10/2003 | Russo |
| 2003/0199835 A1 | 10/2003 | Leinsing et al. |
| 2003/0208165 A1 | 11/2003 | Christensen et al. |
| 2003/0209681 A1 | 11/2003 | Leinsing et al. |
| 2003/0216712 A1 | 11/2003 | Kessler et al. |
| 2003/0225379 A1 | 12/2003 | Schaffer et al. |
| 2003/0236497 A1 | 12/2003 | Fremming et al. |
| 2004/0006330 A1 | 1/2004 | Fangrow |
| 2004/0019344 A1 | 1/2004 | Peterson et al. |
| 2004/0030321 A1 | 2/2004 | Fangrow |
| 2004/0068238 A1 | 4/2004 | Utterberg et al. |
| 2004/0068239 A1 | 4/2004 | Utterberg |
| 2004/0073174 A1 | 4/2004 | Lopez |
| 2004/0073176 A1 | 4/2004 | Utterberg |

| | | |
|---|---|---|
| 2004/0092886 A1 | 5/2004 | Mayer |
| 2004/0102738 A1 | 5/2004 | Dikeman et al. |
| 2004/0111078 A1 | 6/2004 | Miyahara |
| 2004/0116869 A1 | 6/2004 | Heinz et al. |
| 2004/0122418 A1 | 6/2004 | Voorhees |
| 2004/0124388 A1 | 7/2004 | Kiehne |
| 2004/0124389 A1 | 7/2004 | Phillips |
| 2004/0138641 A1 | 7/2004 | Patzer |
| 2004/0162517 A1 | 8/2004 | Furst et al. |
| 2004/0162540 A1 | 8/2004 | Walenciak et al. |
| 2004/0171993 A1 | 9/2004 | Bonaldo |
| 2004/0172006 A1 | 9/2004 | Bonaldo |
| 2004/0186458 A1 | 9/2004 | Hiejima et al. |
| 2004/0193119 A1 | 9/2004 | Canaud et al. |
| 2004/0199126 A1 | 10/2004 | Harding et al. |
| 2004/0204699 A1 | 10/2004 | Hanly et al. |
| 2004/0206924 A1 | 10/2004 | Newton et al. |
| 2004/0210194 A1 | 10/2004 | Bonnette et al. |
| 2004/0225274 A1 | 11/2004 | Jansen et al. |
| 2004/0227120 A1 | 11/2004 | Raybuck |
| 2004/0236314 A1 | 11/2004 | Saab |
| 2004/0243065 A1 | 12/2004 | McConnell et al. |
| 2004/0243069 A1 | 12/2004 | Feith et al. |
| 2004/0243070 A1 | 12/2004 | Lopez |
| 2004/0249349 A1 | 12/2004 | Wentling |
| 2004/0254534 A1 | 12/2004 | Bjorkman et al. |
| 2004/0260243 A1 | 12/2004 | Rickerd |
| 2004/0260266 A1 | 12/2004 | Cuschieri et al. |
| 2005/0010168 A1 | 1/2005 | Kendall |
| 2005/0015070 A1 | 1/2005 | Delnevo et al. |
| 2005/0021000 A1 | 1/2005 | Adair et al. |
| 2005/0033267 A1 | 2/2005 | Decaria |
| 2005/0033268 A1 | 2/2005 | Decaria |
| 2005/0033269 A1 | 2/2005 | Decaria |
| 2005/0038397 A1 | 2/2005 | Newton et al. |
| 2005/0059952 A1 | 3/2005 | Giuliano et al. |
| 2005/0087715 A1 | 4/2005 | Doyle |
| 2005/0090805 A1 | 4/2005 | Shaw et al. |
| 2005/0096585 A1 | 5/2005 | Schon et al. |
| 2005/0107770 A1 | 5/2005 | Schweikert et al. |
| 2005/0119613 A1 | 6/2005 | Moenning et al. |
| 2005/0121638 A1 | 6/2005 | Doyle |
| 2005/0124935 A1 | 6/2005 | McMichael |
| 2005/0124942 A1 | 6/2005 | Richmond |
| 2005/0124943 A1 | 6/2005 | Yang |
| 2005/0154372 A1 | 7/2005 | Minezaki |
| 2005/0159710 A1 | 7/2005 | Utterberg |
| 2005/0165365 A1 | 7/2005 | Newton et al. |
| 2005/0171487 A1 | 8/2005 | Haury et al. |
| 2005/0209555 A1 | 9/2005 | Middleton et al. |
| 2005/0228362 A1 | 10/2005 | Vaillancourt |
| 2005/0256460 A1 | 11/2005 | Rome et al. |
| 2005/0256461 A1 | 11/2005 | DiFiore et al. |
| 2005/0261637 A1 | 11/2005 | Miller |
| 2005/0261665 A1 | 11/2005 | Voorhees |
| 2005/0267445 A1 | 12/2005 | Mendels |
| 2006/0015086 A1 | 1/2006 | Rasmussen et al. |
| 2006/0025724 A1 | 2/2006 | Chen |
| 2006/0025751 A1 | 2/2006 | Roy et al. |
| 2006/0027270 A1 | 2/2006 | Truitt et al. |
| 2006/0047251 A1 | 3/2006 | Bickford-Smith et al. |
| 2006/0074386 A1 | 4/2006 | Wollmann |
| 2006/0089603 A1 | 4/2006 | Truitt et al. |
| 2006/0089604 A1 | 4/2006 | Guerrero |
| 2006/0089605 A1 | 4/2006 | Fitzgerald |
| 2006/0111694 A1 | 5/2006 | Fukai et al. |
| 2006/0129109 A1 | 6/2006 | Shaw et al. |
| 2006/0129112 A1 | 6/2006 | Lynn |
| 2006/0142735 A1 | 6/2006 | Whitley |
| 2006/0149213 A1 | 7/2006 | Raybuck |
| 2006/0161115 A1 | 7/2006 | Fangrow |
| 2006/0173420 A1 | 8/2006 | Fangrow |
| 2006/0178645 A1 | 8/2006 | Peppel |
| 2006/0184139 A1 | 8/2006 | Quigley et al. |
| 2006/0184140 A1 | 8/2006 | Okiyama |
| 2006/0200072 A1 | 9/2006 | Peppel |
| 2006/0200095 A1 | 9/2006 | Steube |
| 2006/0200096 A1 | 9/2006 | Fangrow |
| 2006/0206058 A1 | 9/2006 | Lopez |
| 2006/0206059 A1 | 9/2006 | Lopez |
| 2006/0211997 A1 | 9/2006 | Fangrow |
| 2006/0211998 A1 | 9/2006 | Fangrow |
| 2006/0211999 A1 | 9/2006 | Fangrow |
| 2006/0212000 A1 | 9/2006 | Fangrow |
| 2006/0212001 A1 | 9/2006 | Fangrow |
| 2006/0212002 A1 | 9/2006 | Fangrow |
| 2006/0212003 A1 | 9/2006 | Fangrow |
| 2006/0212005 A1 | 9/2006 | Fangrow |
| 2006/0212006 A1 | 9/2006 | Fangrow et al. |
| 2006/0217671 A1 | 9/2006 | Peppel |
| 2006/0217679 A1 | 9/2006 | Hanly et al. |
| 2006/0217683 A1 | 9/2006 | Patania |
| 2006/0229571 A1 | 10/2006 | Peppel |
| 2006/0229590 A1 | 10/2006 | Roy |
| 2006/0264842 A1 | 11/2006 | Fangrow |
| 2006/0264843 A1 | 11/2006 | Fangrow |
| 2006/0264844 A1 | 11/2006 | Fangrow |
| 2006/0264845 A1 | 11/2006 | Lopez |
| 2006/0264846 A1 | 11/2006 | Lopez |
| 2006/0264847 A1 | 11/2006 | Lopez |
| 2006/0264848 A1 | 11/2006 | Fangrow |
| 2006/0264890 A1 | 11/2006 | Moberg et al. |
| 2006/0264891 A1 | 11/2006 | Lopez |
| 2006/0264892 A1 | 11/2006 | Lopez |
| 2006/0264894 A1 | 11/2006 | Moberg et al. |
| 2006/0264908 A1 | 11/2006 | Ishii et al. |
| 2006/0264909 A1 | 11/2006 | Fangrow |
| 2006/0264910 A1 | 11/2006 | Fangrow |
| 2006/0270999 A1 | 11/2006 | Fangrow |
| 2006/0271012 A1 | 11/2006 | Canoud |
| 2006/0271015 A1 | 11/2006 | Mantell |
| 2006/0271016 A1 | 11/2006 | Fangrow |
| 2006/0276757 A1 | 12/2006 | Fangrow |
| 2006/0276758 A1 | 12/2006 | Fangrow |
| 2006/0287638 A1 | 12/2006 | Aneas |
| 2006/0287639 A1 | 12/2006 | Sharp |
| 2006/0293629 A1 | 12/2006 | Cote et al. |
| 2006/0293640 A1 | 12/2006 | Greco |
| 2007/0032775 A1 | 2/2007 | Niedospial et al. |
| 2007/0032776 A1 | 2/2007 | Skinner et al. |
| 2007/0038189 A1 | 2/2007 | Bartholomew |
| 2007/0043334 A1 | 2/2007 | Guala |
| 2007/0060898 A1 | 3/2007 | Shaughnessy et al. |
| 2007/0060902 A1 | 3/2007 | Brandenburger et al. |
| 2007/0060904 A1 | 3/2007 | Vedrine et al. |
| 2007/0073242 A1 | 3/2007 | Andersen et al. |
| 2007/0078393 A1 | 4/2007 | Lynch et al. |
| 2007/0078429 A1 | 4/2007 | Sharp |
| 2007/0083157 A1 | 4/2007 | Belley et al. |
| 2007/0088252 A1 | 4/2007 | Pestotnik et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0088313 A1 | 4/2007 | Zinger et al. |
| 2007/0088324 A1 | 4/2007 | Fangrow |
| 2007/0088325 A1 | 4/2007 | Fangrow |
| 2007/0088327 A1 | 4/2007 | Guala |
| 2007/0093764 A1 | 4/2007 | Guerrero |
| 2007/0100294 A1 | 5/2007 | Sugita et al. |
| 2007/0112311 A1 | 5/2007 | Harding et al. |
| 2007/0112312 A1 | 5/2007 | Fangrow |
| 2007/0112313 A1 | 5/2007 | Fangrow |
| 2007/0112314 A1 | 5/2007 | Harding et al. |
| 2007/0112332 A1 | 5/2007 | Harding et al. |
| 2007/0112333 A1 | 5/2007 | Hoang et al. |
| 2007/0129705 A1 | 6/2007 | Trombley et al. |

| | | |
|---|---|---|
| 2007/0156112 A1 | 7/2007 | Walsh |
| 2007/0156118 A1 | 7/2007 | Ramsey et al. |

FOREIGN PATENT DOCUMENTS

| | | |
|---|---|---|
| DE | 855319 | 11/1952 |
| DE | 8425197 | 10/1985 |
| DE | 3740269 | 6/1989 |
| EP | 0114677 | 8/1984 |
| EP | 0237321 | 9/1987 |
| EP | 0309771 | 4/1989 |
| EP | 0367549 | 10/1989 |
| EP | 0399119 | 11/1990 |
| EP | 0438909 | 12/1990 |
| EP | 0446463 | 12/1990 |
| EP | 1733749 A1 | 12/2006 |
| GB | 2034185 | 6/1980 |
| WO | 86/01712 | 3/1986 |
| WO | 86/03416 | 6/1986 |
| WO | 93/11828 | 6/1993 |
| WO | 97/21463 | 6/1997 |
| WO | 97/21464 | 6/1997 |
| WO | 98/26835 | 6/1998 |
| WO | 99/58186 | 11/1999 |
| WO | 02/04065 | 1/2002 |
| WO | 03/086528 | 10/2003 |

* cited by examiner

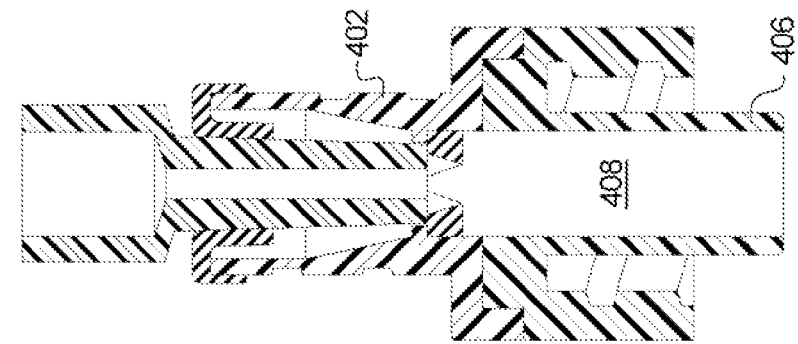
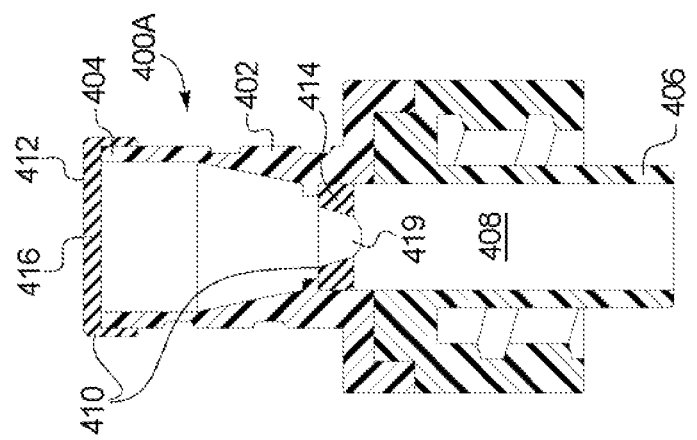
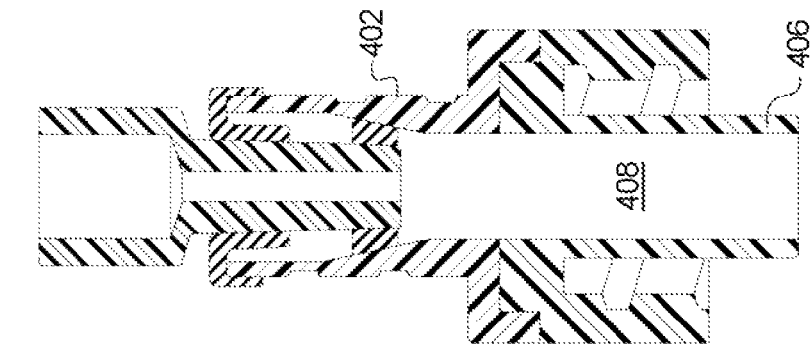
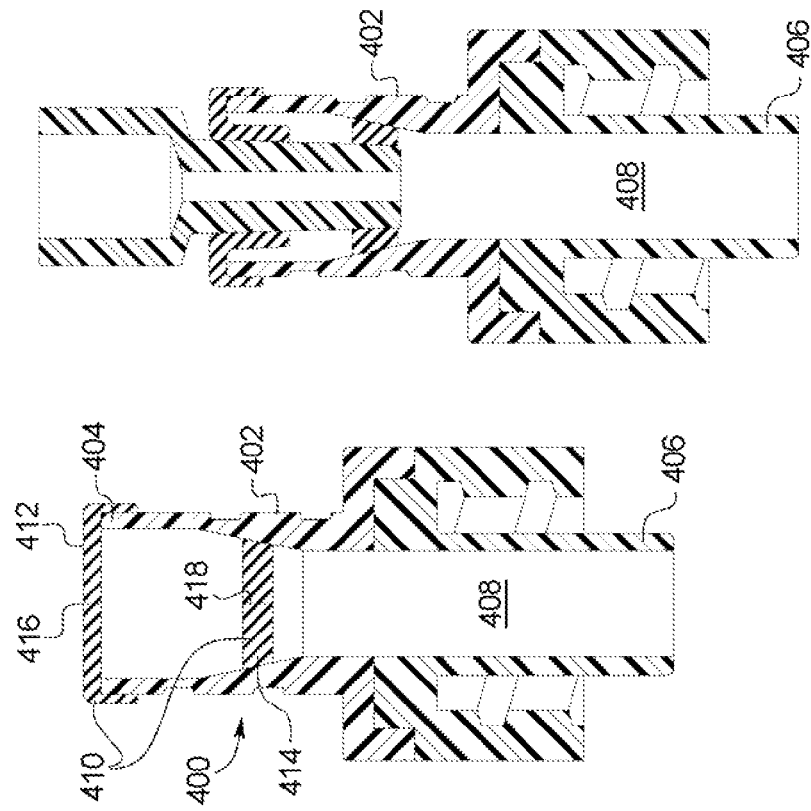

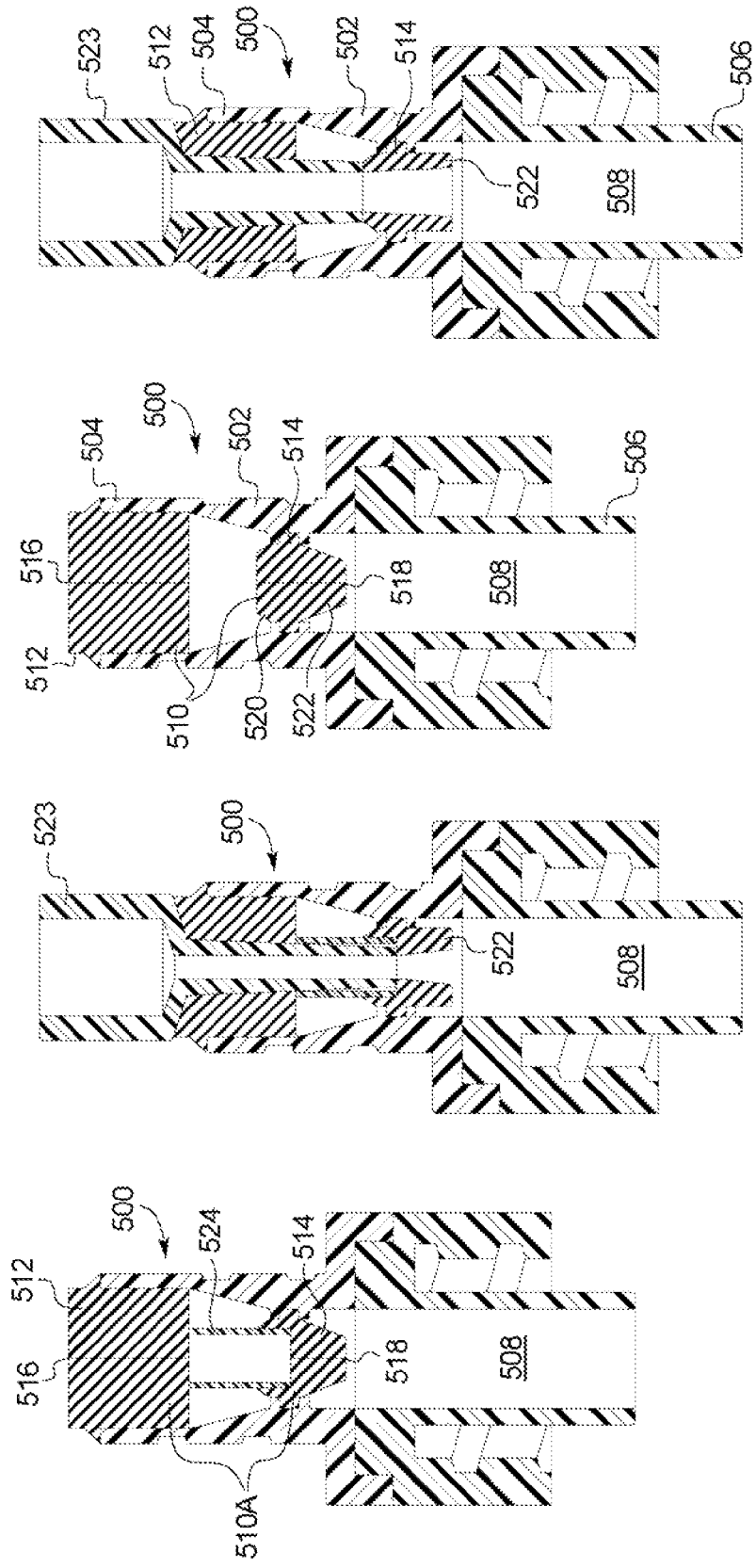

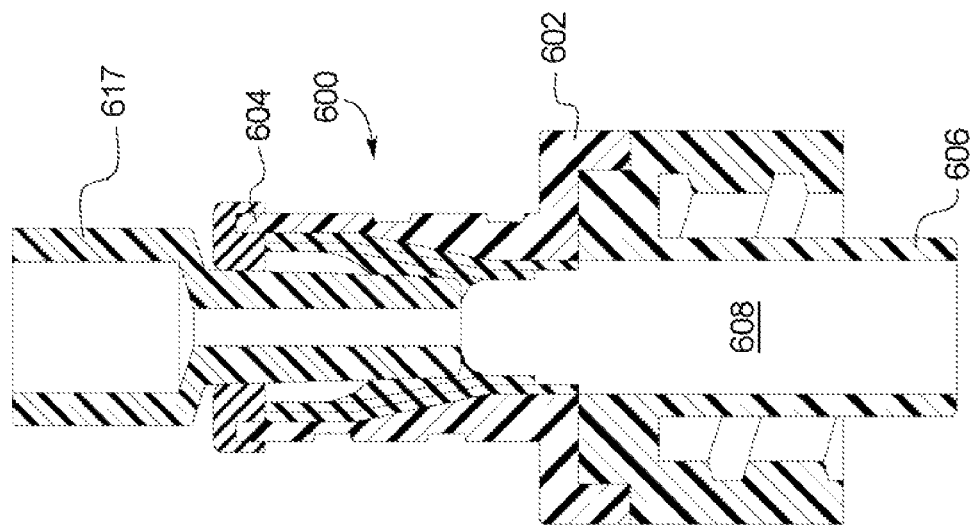
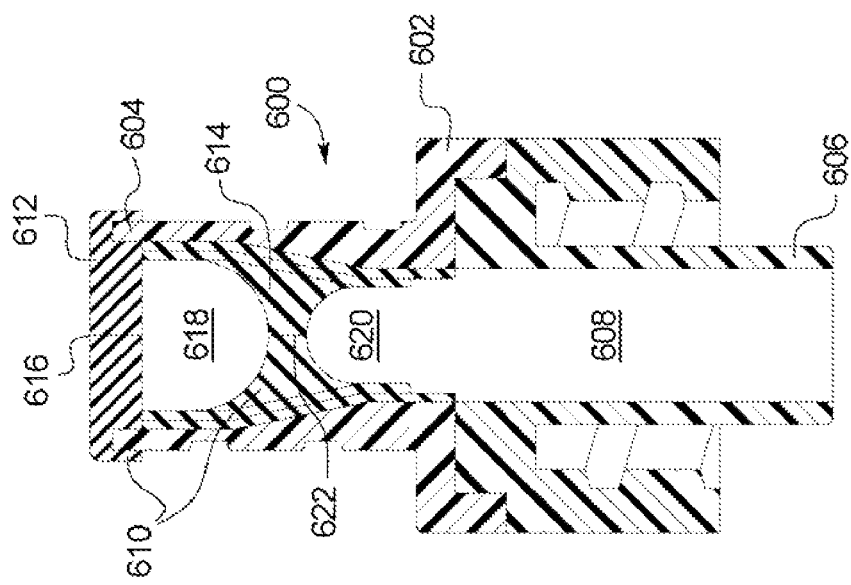

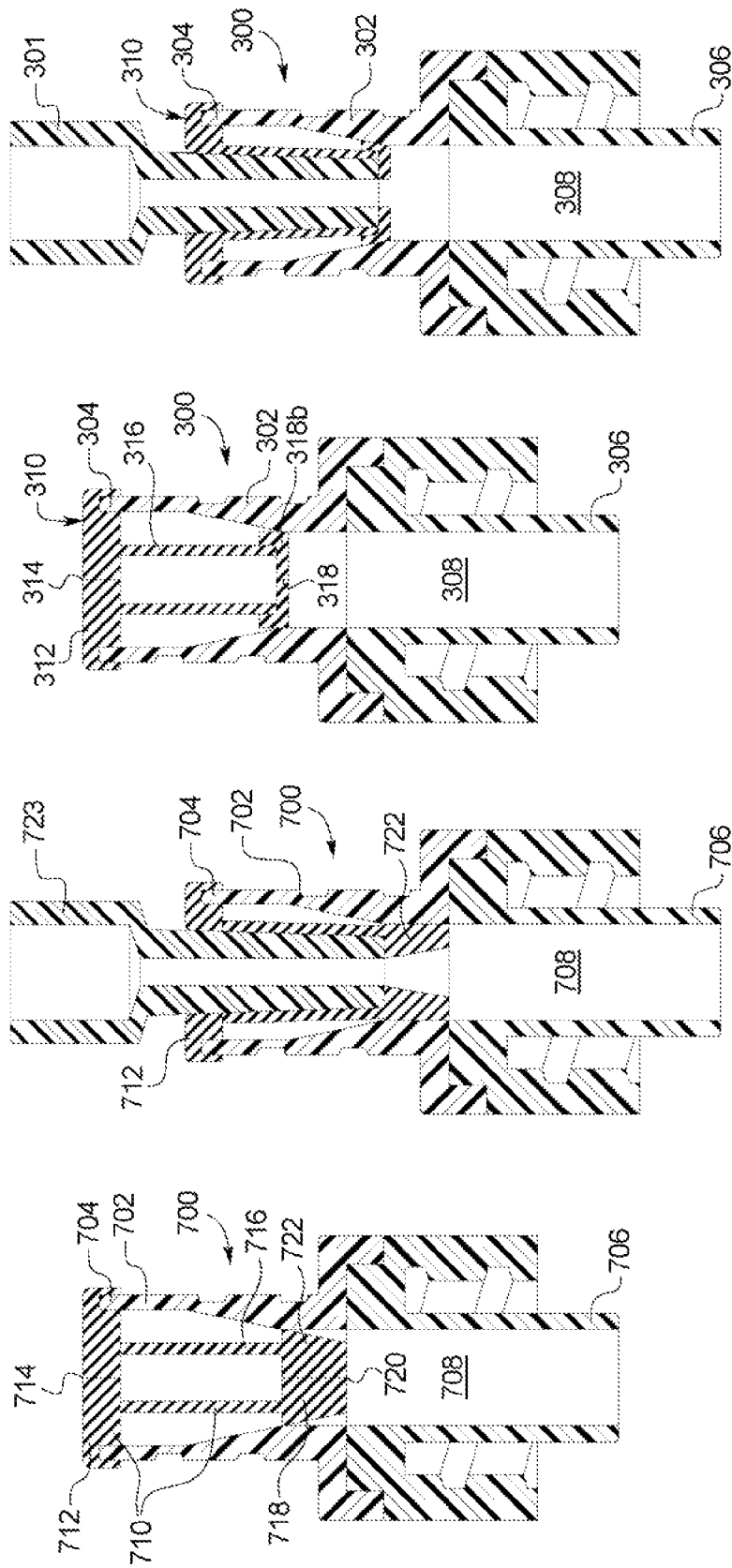

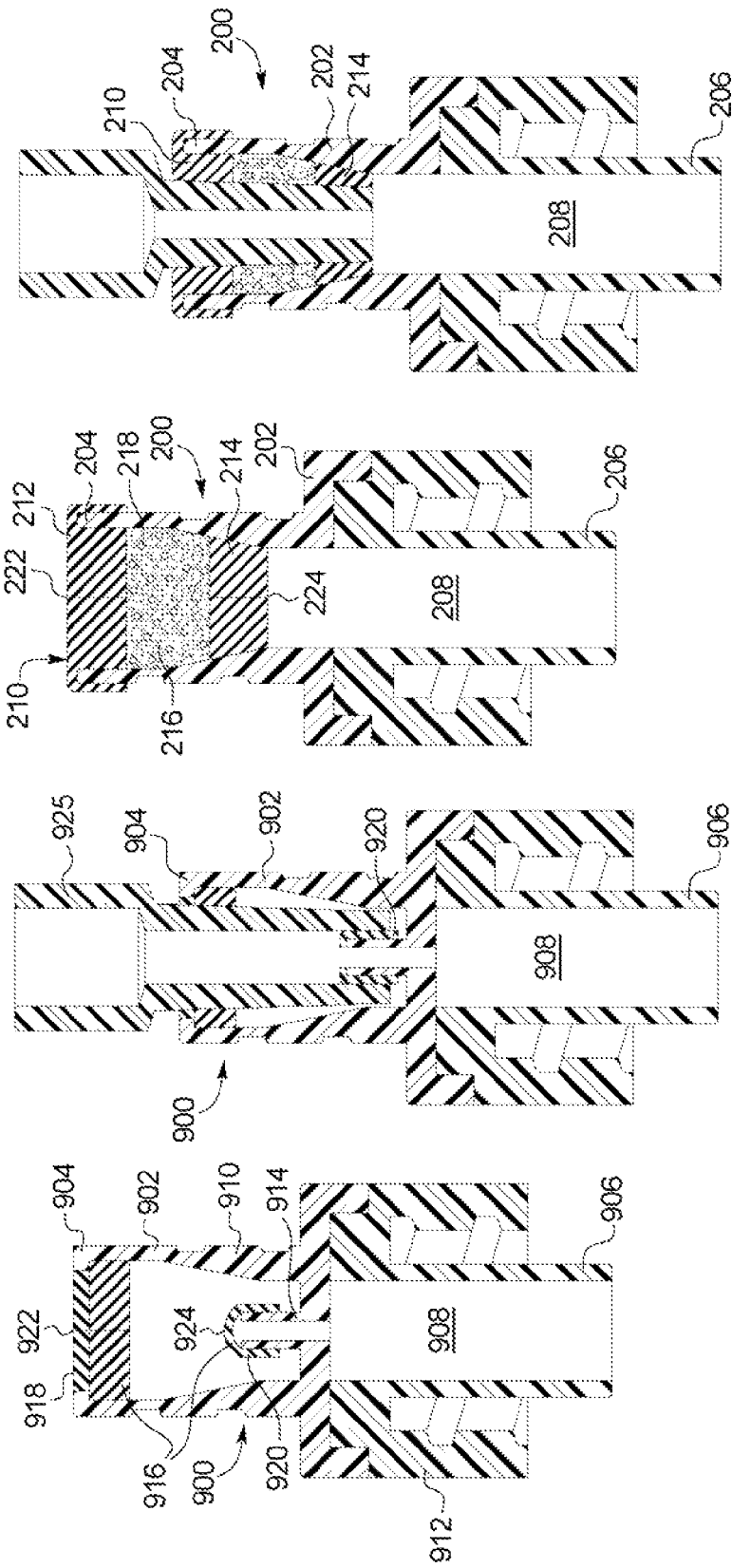

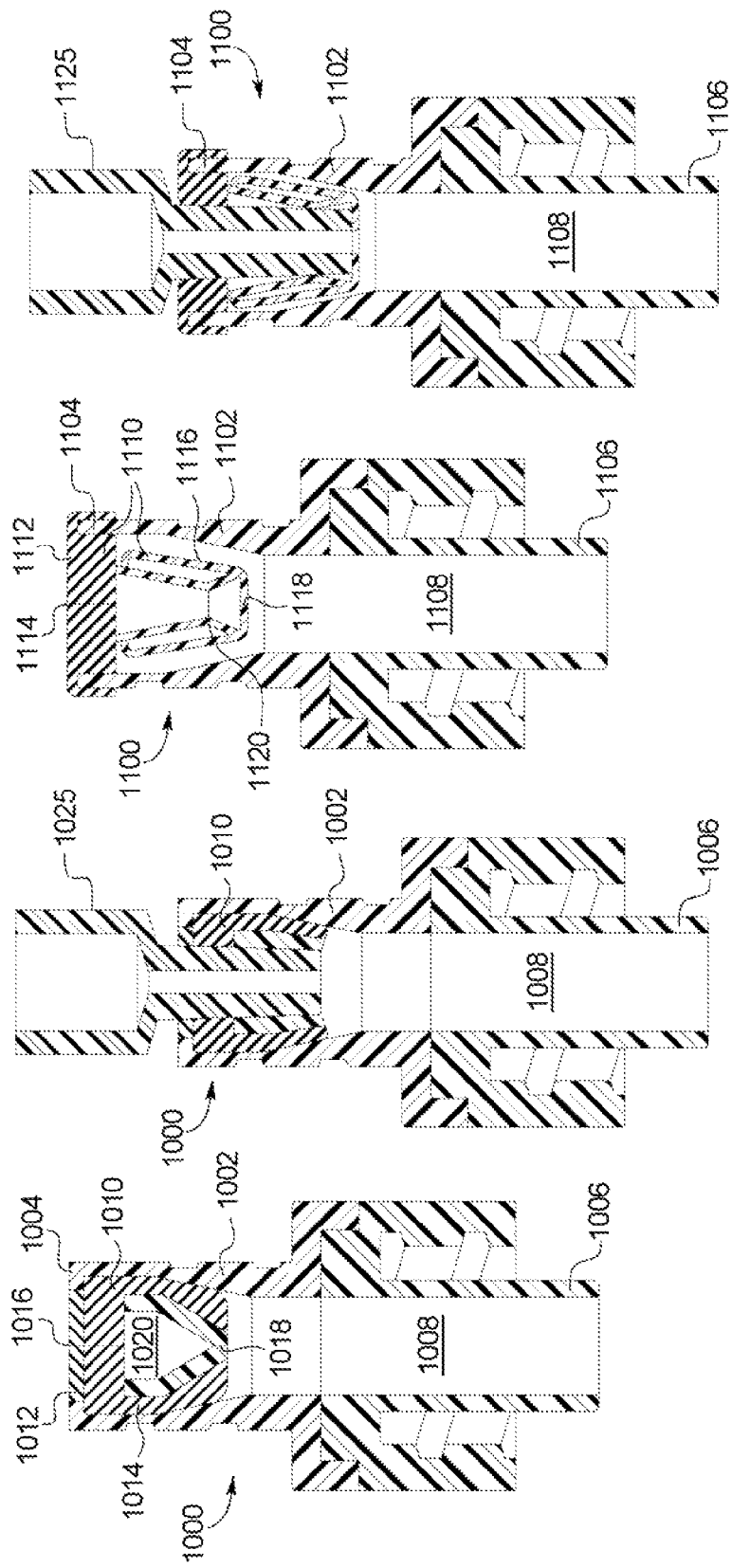

LUER ACTIVATED DEVICE WITH MINIMAL FLUID DISPLACEMENT

PRIORITY CLAIM

This application claims the benefit of U.S. Provisional Patent Application No. 60/862,502, filed Oct. 23, 2006, entitled "LUER ACTIVATED DEVICE WITH MINIMAL FLUID DISPLACEMENT", the entire contents of which are hereby incorporated by reference and relied upon.

FIELD OF THE INVENTION

The present invention relates generally to luer activated devices or valves that allow for the bi-directional transfer of fluids to and from medical fluid flow systems.

BACKGROUND OF THE INVENTION

Luer activated devices (LAD) or valves (LAV) are commonly used in association with medical fluid containers and medical fluid flow systems that are connected to patients or other subjects undergoing diagnostic, therapeutic or other medical procedures. A LAD can be attached to or part of a fluid container or a medical fluid flow system to simplify the addition of fluids to or withdrawal of fluids from the fluid flow system.

Within the medical field there are a wide variety of medical fluid flow systems, serving a variety of functions. One of the more common uses of LADs are in association with fluid flow systems that are used for the intravenous administration of fluids, such as saline, antibiotics, or any number of other medically-related fluids, to a patient. These flow systems are commonly referred to as intravenous or "IV" fluid administration sets, and use plastic tubing to connect a phlebotomized subject to one or more medical fluid sources, such as intravenous solution or medicament containers.

Typically, such intravenous administration sets include one or more LADs providing needless access to the fluid flow path to allow fluid to be added to or withdrawn from the IV tubing. The absence of a needle for injecting or withdrawing fluid has the important advantage of reducing the incidence of needle stick injuries to medical personnel. A LAD typically includes a tapered female luer component, such as the inlet into a valve housing, that accepts and mates with a tapered male luer of a medical infusion or aspiration device, such as a needleless syringe or a administration set tubing brand.

There are certain characteristics and qualities of LADs that are highly desirable. For example, the LAD should provide a sufficient microbial barrier for the full service life of the valve. It is desirable that the microbial barrier be conducive to the application of standard aseptic techniques preformed by clinicians during the use of the device. For example, the geometry of the LAD should be such that it is easily swabbable and reduces the potential of entrapping particulates or contaminants that cannot be cleanly swabbed clear prior to use.

Furthermore, it is highly desirable that the LAD be substantially devoid of any interstitial space or any other "dead space" that cannot be flushed, or that such interstitial space be physically isolated from the fluid flow path. Such interstitial space has the potential of providing an environment for undesired microbial growth. In addition, the LAD should have a geometry that allows it to be sufficiently flushed so as to clear the dynamic fluid path and adjacent areas of residual blood or intravenous fluids to prevent undesired clotting or microbial growth.

LAD's are commonly used with intravenous catheters that provide access to a patient's vascular system. In such systems, another desirable feature of a LAD is minimal displacement of fluid during insertion and removal of the male luer. In certain situations, it is preferable that the LAD be a neutral/neutral device in that there is zero or only a very slight displacement of fluid during both insertion and removal of the male luer. In other situations it can be desirable for the LAD to produce a positive displacement of fluid from the valve housing during the removal of the male luer. The LAD also preferably prevents blood reflux into the catheter. Reflux is known to reduce the efficiency of the catheter and contribute to catheter clotting.

In most situations it is preferred that the LAD be dimensioned to be completely activated by a wide range of ISO compliant male luer lock adaptors. However, there may be some instances when the LAD may be designed to be activated by a male luer connector that is not ISO complaint or is a male luer slip connector. Another desirable characteristic of a LAD is the ability of the LAD to seal against pressure contained within a fluid system to which the LAD is connected. For example, it is desirable to be leak resistance to positive pressures ranging from 10 to 45 psi and to negative pressures or vacuum from 1 to 5 psi. The LAD also preferably has a geometry that allows for easy priming and flushing that does not require any additional manipulations to remove residual air bubbles from the tubing system.

These and other desirable characteristics, which may be used separately or in various combinations, are preferably present over the full service life of the valve. When used in connection with an IV set or catheter, the LAD may go through many connections and disconnections. It is desirable that the life of a LAD last through upwards to about 100 connections and disconnections or 96 hours of dwell time.

As described more fully below, the fluid access devices of the present invention provide important advances in the safe and efficient administration or withdrawal of medical fluids to or from a fluid flow system.

SUMMARY OF THE INVENTION

In accordance with one aspect of the present invention, a luer activated medical valve for the bi-directional transfer of fluid therethrough is provided with a valve housing having an inlet adapted to receive a male luer, an outlet, and a flow path defined therebetween. A valve element is received within the inlet of the valve housing and includes a resealable aperture adapted to receive a male luer to allow fluid to be transferred between the male luer and the flow path. In accordance with one aspect of this invention, when the male luer is inserted or removed from the aperture, there is substantially no fluid displacement from or into the valve housing.

BRIEF DESCRIPTION OF THE DRAWINGS

Turning now to a more detailed description of the various embodiments of the present invention illustrated in the attached drawings, of which:

FIG. 9 is a cross-sectional view of a LAD having a valve element with two septa according to an aspect of the present invention;

FIG. 10 is a cross-sectional view of the LAD of FIG. 7, in an open condition;

FIG. 11 is a cross-sectional view of a LAD having a septa with a cusp valve;

FIG. 12 is a cross-sectional view of the LAD of FIG. 11, with the cusp valve in an open condition;

FIG. 13 is a cross-sectional view of a LAD having a valve element with a septum and a split-leg opening valve casing joined by a channel, in a closed condition;

FIG. 14 is a cross-sectional view of the LAD of FIG. 13, with the split-leg opening valve casing in an open condition;

FIG. 15 is a cross-sectional view of a LAD having a valve element with a split-leg opening valve casing, in a closed condition;

FIG. 16 is a cross-sectional view of the LAD of FIG. 15, with the split-leg opening valve casing in an open condition;

FIG. 17 is a cross-sectional view of a LAD having a valve element with a pair of void volumes;

FIG. 18 is a cross-sectional view of the LAD of FIG. 17, in an open condition;

FIG. 19 is a cross-sectional view of a LAD having a valve element with a barbed void volume arrow;

FIG. 20 is a cross-sectional view of the LAD of FIG. 19, in an open condition;

FIG. 21 is a cross-sectional view of a LAD having a valve element with a low pressure seal cap;

FIG. 22 is a cross-sectional view of the LAD of FIG. 21, in an open condition;

FIG. 27 is a cross-sectional view of a LAD having a valve element with a stand pipe surrounded by an over sleeve;

FIG. 28 is a cross-sectional view of the LAD of FIG. 27, in an open condition;

FIG. 29 is a cross-sectional view of an alternate embodiment of the LAD of FIG. 5, in a closed condition;

FIG. 30 is a cross-sectional view of the LAD of FIG. 29, in an open condition;

FIG. 31 is a cross-sectional view of a LAD having a valve element with a plurality of sealing flanges;

FIG. 32 is a cross-sectional view of the LAD of FIG. 29, in an open condition;

FIG. 33 is a cross-sectional view of a LAD having a valve element with a cammed seal cap; and FIG. 34 is a cross-sectional view of the LAD of FIG. 33, in an open condition.

DETAILED DESCRIPTION OF THE INVENTION

The embodiments disclosed herein are for the purpose of providing the required description of the present invention. These embodiment, however, are exemplary of the invention, which may be embodied in various forms. Therefore, specific details disclosed herein are not to be interpreted as limiting the invention as defined in the accompanying claims.

Figure 2:
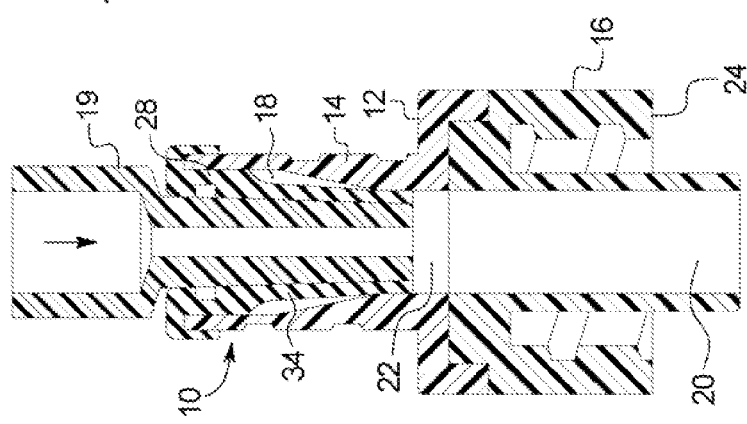
FIG. 2 is a cross-sectional view of the LAD of FIG. 1, in an open condition
Figure 1:
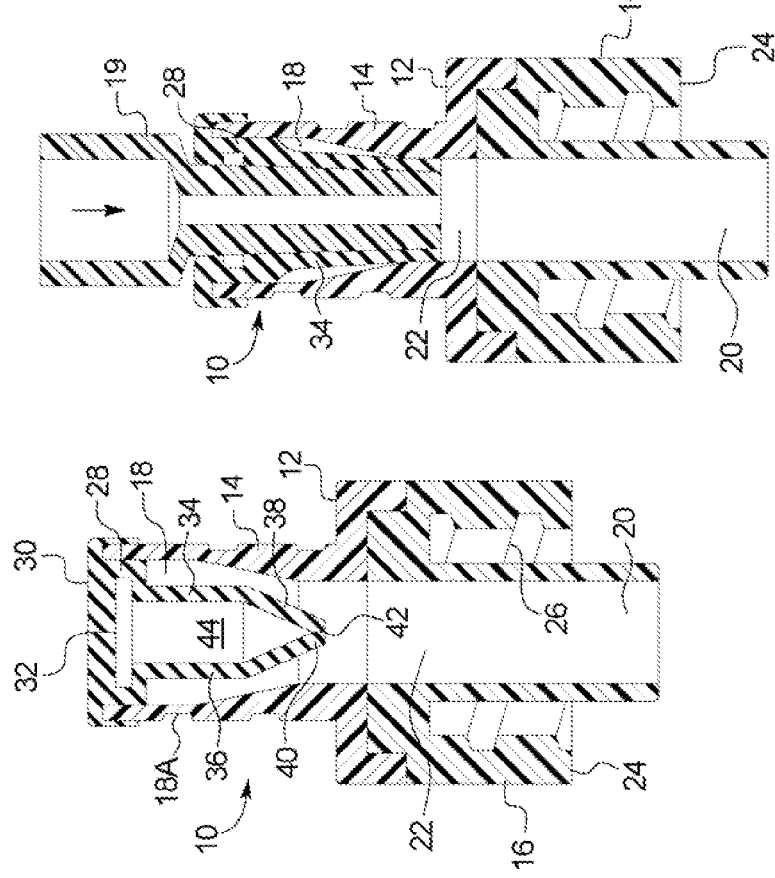
FIG. 1 is a cross-sectional view of one embodiment of a luer activated device having a valve element with a two-way blunt nose slit valve design.

FIGS. 1 and 2 generally illustrates a first embodiment of a luer activated device (LAD) or valve of the present invention, generally designated as 10. The LAD 10 includes a valve housing 12 preferably comprised of a rigid material, such as rigid plastic or other suitable material. The LAD 10 may be provided as a unitary structure (not illustrated) or as a combination of a joined upper housing portion 14 and a lower housing portion 16. The LAD 10 also includes an inlet 18, an outlet 20, and a flow path 22 defined therebetween. The terms "inlet" and "outlet" are not to be interpreted as limiting the LAD 10 to applications involving fluid flow in a particular direction, e.g., from the inlet 18 to the outlet 20, because LAD's according to the present invention may be used in applications involving fluid flow from the inlet 18 to the outlet 20 or from the outlet 20 to the inlet 18.

The outlet 20 is adapted to be connected to any of a number of fluid flow systems, so the exact configuration of the outlet 20 will vary according to the nature of the fluid flow system to which it is to be connected. For example, the illustrated outlet 20 is suitable for use in connecting the valve 10 to an IV administrative tubing set (not illustrated). In the embodiment of FIG. 1, the outlet 20 may have a standard tapered male luer configuration and include a collar 24 defining an internal thread 26, which may be adapted to engage an external thread of the associated fluid flow system (not illustrated). Of course, the outlet 20 may be provided with a different configuration, a different locking system, or without a locking system, depending on the anticipated usage of the valve 10. Also, the valve 10 may be formed as an integral part of a larger structure without departing from the present invention.

The inlet 18 is adapted to receive a male connector such as a standard male luer 19 according to known structure and operation. The inlet 18 and male luer 19 preferably conform to ISO and/or ANSI standards. The male luer is generally tubular and preferably has a substantially smooth outer surface which is typically slightly tapered. The inlet 18 may include external threads 18a, in which case a portion of the connecting luer may be surrounded by a collar or skirt member (not illustrated) having internal threads adapted to removably lock the male luer to the inlet 18. Other attachment mechanisms, such frictional engagement with a tapered luer slip fit 19 may also be incorporated into LAD's according to the present invention.

To control flow through the housing 12, a valve system or element 28 is provided with a deformable upper seal or septum 30 defining a normally closed resealable first aperture 32 (preferably but not exclusively in the form of a slit) therethrough. The upper seal 30 is fixedly mounted to normally block and seal the inlet 18. A hollow blunt extension 34 extends downwardly from the upper seal 30 and communicates with the first aperture 32. Preferably, the extension 34 is comprised of a generally tubular portion 36, a generally conical or tapered portion 38, and a lower seal or septum portion 40 defining a generally blunt nose end with a second normally closed resealable aperture 42 therethrough. An internal chamber 44 is defined by the valve element 28 and connects the apertures 32 and 42. The chamber 44 is normally closed or isolated from the flow path 22 when the second aperture 42 is in a closed condition. The valve element 28 thus acts as a microbial barrier between the internal fluid flow path 22 of the LAD 10 and the atmosphere and substantially prevents fluid displacement when a luer is inserted into or removed from the LAD 10, as will be described in greater detail herein.

Preferably, the valve element 28 is molded as a unitary piece, typically from a deformable elastomeric material, such as silicone or rubber or Santoprene® thermoplastic, manufactured by Advanced Elastomer Systems, LP of Akron, Ohio. The valve element 28 may be fixedly attached to the inlet 18 by any of a number of means. Suitable means include, but are not limited to, adhesive or mechanical bonding and interference overmolding. At the inlet, the upper seal 30 preferably has a substantially flat or slightly outwardly curved outside surface that can be easily wiped with antiseptic, which aids in preventing contamination during use. The apertures 32 and 42 may be integrally formed, e.g., molded, with the seals 30 and 40 or may be formed after the valve element 28 is manufactured or seated within the inlet 18, such as by a slitting operation.

In use, a male luer 19 is inserted into the inlet 18 through the first aperture 32, which causes deformation of the valve element 28. The valve element 28 continues to deform as the luer is further inserted into the inlet 18 and, in a preferred embodiment, the lower seal portion 40 is adapted to deform and open the second aperture 42 substantially concurrently with full insertion of the male luer for insertion or withdrawal of liquid. To avoid fluid displacement as the luer is inserted into or removed from the inlet 18, upon full insertion of the male luer 19 the distance between the apertures 32 and 42 is preferably greater than the maximum extent to which the luer may be inserted into the inlet 18. By such a configuration, a fully inserted luer will remain almost wholly within the chamber 44. Accordingly, only a small portion of the luer may enter the LAD flow path 22 and decrease the available open volume, so fluid displacement upon insertion and removal of the luer is substantially neutralized.

In one embodiment, the blunt nose tubular portion 36 deforms outwardly by the force of the male luer to be in close proximity of the wall of the inlet 18, which reduces that volume of the LAD 10 as a possible fluid stagnation region or dead zone. While this tends to decrease the volume of the flow path 22, this change in volume is minor, especially compared to prior art valves which cause the luer to be fully inserted into the flow path, so fluid displacement with respect to the outlet 20 during insertion and removal of the luer is insignificant.

Figure 4:
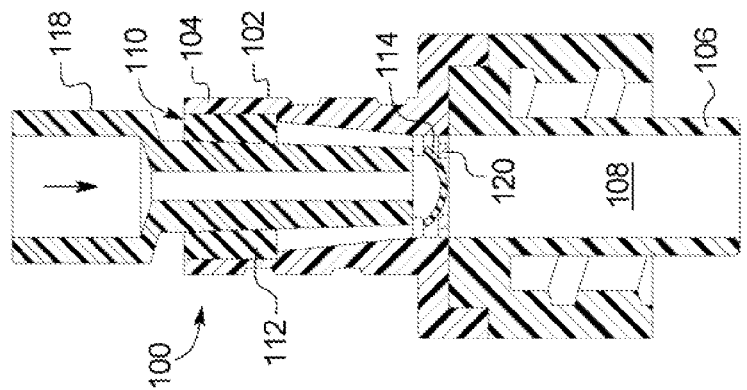
FIG. 4 is a cross-sectional view of the LAD of FIG. 3, with the umbrella valve in an open condition.
Figure 3:
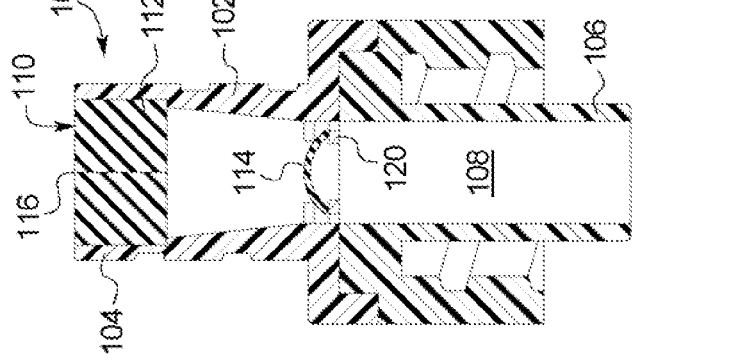
FIG. 3 is a cross-sectional view of an LAD having a valve element with a bi-directional umbrella valve, in a closed condition.

FIGS. 3 and 4 illustrate another embodiment of a LAD 100 according to the present invention. The LAD 100 includes a valve housing 102, an inlet 104, an outlet 106, and a flow path 108 generally according to the foregoing description of the embodiment of FIG. 1. A valve element 110 is received within the inlet 104 to define a barrier between the flow path 108 and the outside environment. The valve element 110 comprises an upper seal 112 and a bi-directional umbrella disc or valve 114 spaced below the upper seal 112.

The upper seal 112 and umbrella valve 114 are deformable, with the upper seal 112 preferably comprising an elastomeric material having a relatively low durometer, such as silicone or rubber or Santoprene® elastomer, and the umbrella valve 114 comprising a more rigid but still flexible material, such as a relatively high durometer silicone.

The upper seal 112 defines a normally closed resealable aperture or slit 116 adapted to receive a male luer 118. The upper seal 112 preferably conforms generally to the description of the upper seal 30 of the embodiment of FIG. 1.

In the illustrated embodiment, the peripheral edge of the umbrella valve 114 seats on an annular shoulder 120 of the housing 102 and is maintained in place by stop means (not illustrated), but it may cooperate with alternative housing features, such as an annular channel or the like. The umbrella valve 114 is movable between a downwardly concave closed condition (FIG. 4) and an upwardly concave open condition (FIG. 4). In the closed condition, the umbrella valve 114 resembles a dome and seals fluid communication between the housing flow path 108 and the inlet 104. In the open condition of FIG. 4, the umbrella valve 114 reverses orientation to resemble a cup or saucer and unseats from the annular shoulder 120, thereby opening fluid communication between the housing flow path 108 and the inlet 104. Preferably, the umbrella valve 114 is resiliently biased to the closed condition, such that it will only assume the open condition upon application of an external influence or pressure and will automatically return to the closed condition upon removal of that influence. The transition from the closed condition to the open condition is preferably caused by contact with the male luer 118, as described in greater detail herein.

In use, the male luer 118 is initially inserted into the inlet 104 through the aperture 116. The luer 118 is further inserted until it contacts the umbrella valve 114 and moves the umbrella valve 114 to the open condition of FIG. 4. Preferably, the valve element 110 is adapted such that the umbrella valve 114 will move to the open condition substantially concurrently with the luer 118 being fully inserted into the inlet 104. With the umbrella valve 114 in the open condition, fluid flow may be achieved between the luer 118 and the LAD outlet 106. When the luer 118 is removed from the LAD 100, the umbrella valve 114 snaps back to the closed condition of FIG. 3, thereby closing fluid flow through the LAD 100.

It will be seen that the luer 118 remains above the umbrella valve 114 and outside of the LAD flow path 108 at all times, so the deflection and deformation of the umbrella valve 114 represents the only variation of the flow path 108 volume during insertion and removal of the luer 118. Accordingly, the volume of the flow path 108 remains substantially constant during use of the LAD 100, and fluid displacement upon insertion and removal of the luer 118 is substantially neutralized.

FIGS. 5 and 6 and 29 and 30 illustrates yet another LAD 200 according to the present invention. The LAD 200 includes a valve housing 202, an inlet 204, an outlet 206, and a flow path 208 generally according to the foregoing description of the embodiment of FIG. 1. A valve element 210 is fixedly received within the inlet 204 to define a barrier between the flow path 208 and the outside environment. The valve element 210 comprises an upper seal 212, a lower seal 214, and a spacer member 216 intermediate the upper and lower seals 212 and 214. The valve element 210 acts as a microbial barrier between the internal fluid flow path 208 of the LAD 200 and the atmosphere and substantially prevents fluid displacement when a luer is inserted into or removed from the LAD 200, as will be described in greater detail herein.

Preferably, the valve element 210 is comprised of a deformable elastomeric material, such as silicone or rubber or Santoprene® material. The valve element 210 may be fixedly attached to the inlet 204 by any of a number of means. Suitable means include, but are not limited to, adhesive or mechanical bonding and interference overmolding. Preferably, the spacer member 216 is not affixed to the inlet 204, and may be separated therefrom by a gap or buffer (not illustrated) to allow outward radial movement and deformation of the spacer member 216.

Figure 5:
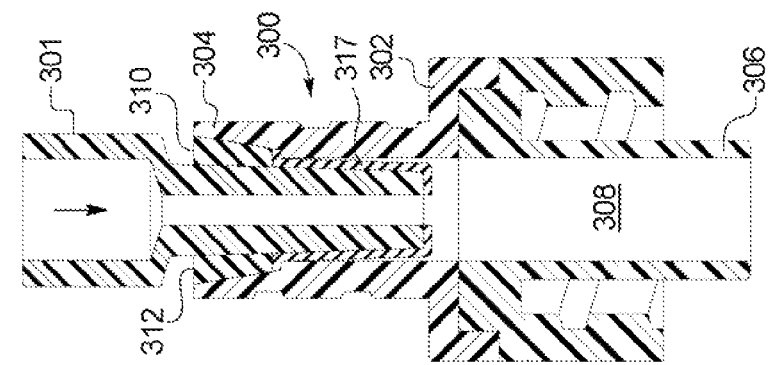
FIG. 5 is a cross-sectional view of a LAD having a valve element with two septa and an elastomeric spacer therebetween.
Figure 6:
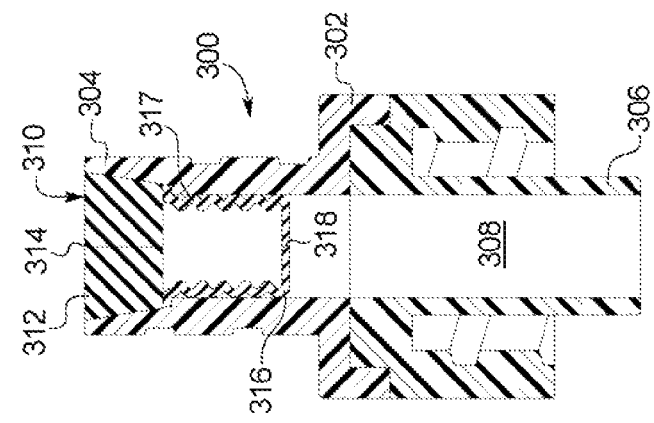
FIG. 6 is a cross-sectional view of the LAD of FIG. 5, in an open condition.

The spacer member 216 may be composed of a foam 218, and referring particularly to FIGS. 5 and 6 may be pre-loaded with an antiseptic or anti-microbial gel or coating 220 to enhance infection control. The volume in which the space member 216 is received is sealed or closed at an upper end by a first resealable slit or aperture 222 in the upper seal 212 and at a lower end by a second resealable slit or aperture 224 in the lower seal 214.

In use, a male luer is inserted into the inlet 204 through the upper aperture 222, which causes deformation of the valve element 210. With the male luer partially inserted into the cavity 218, the spacer member 216 deforms downwardly and outwardly to contact the inlet wall. This deformation of the spacer member 216 is transmitted in part to the lower seal 214, but the lower seal 214 is preferably adapted such that the lower aperture 224 will not deform and open until the luer is fully inserted into the inlet 204.

In an embodiment, the lower seal 214 is sufficiently spaced from the upper seal 212 so that the luer cannot penetrate the lower aperture 224 and enter the LAD flow path 208. Hence, the lower aperture 224 is adapted to open primarily under influence of the deformable spacer member 216, rather than by primarily contact with the luer. When fluid transfer is complete and the luer is moved away from the inlet 204, the lower aperture 224 closes to minimize flow through the LAD 200 and reflux into the housing. As the valve element 210 is adapted to regulate fluid flow through the LAD 200 while minimizing the volume of the luer entering the LAD flow path 208, it will be appreciated that fluid displacement upon insertion and removal of the luer is substantially neutralized.

FIGS. 7-8, and 21-22 and 23-24 illustrate further embodiments of a LAD according to the present invention, generally designated as 300. The LAD 300 includes a valve housing 302, an inlet 304, an outlet 306, and a flow path 308 generally according to the foregoing description of the embodiment of FIG. 1. A valve element 310 is fixedly received within the inlet 304 to define a barrier between the flow path 308 and the outside environment. The valve element 310 comprises a deformable upper seal or septum 312 defining a normally closed resealable first aperture or slit 314 therethrough. The upper seal 312 is comprised of an elastomeric material and fixedly mounted to normally block and seal the inlet 304.

Figure 7:
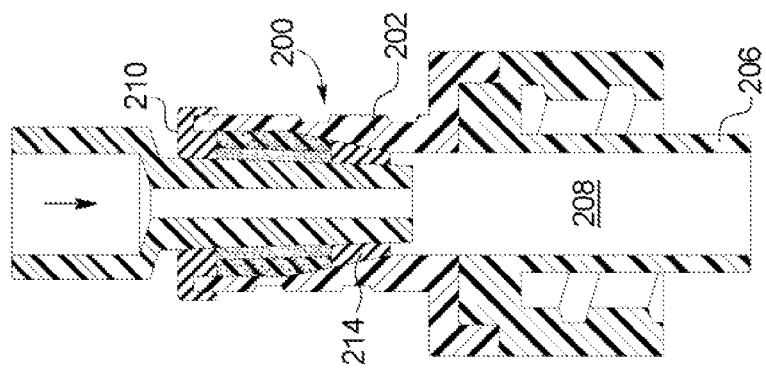
FIG. 7 is a cross-sectional view of a LAD having a valve element with a low pressure seal.
Figure 8:
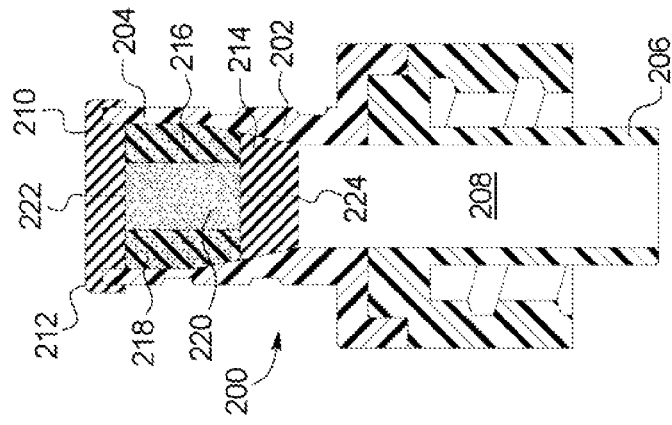
FIG. 8 is a cross-sectional view of the LAD of FIG. 7, with the low pressure seal in an open condition.
Figure 23:
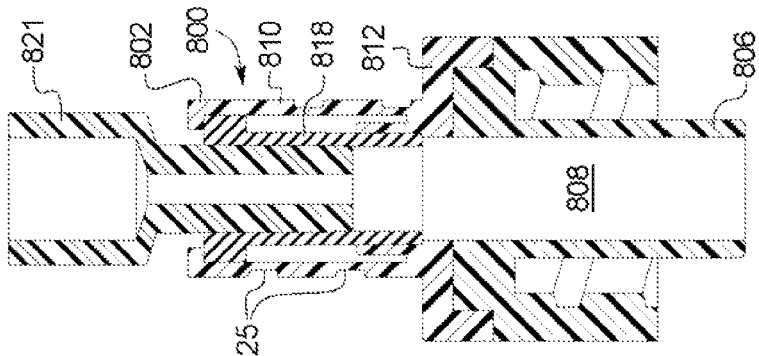
FIG. 23 is a cross-sectional view of a LAD having a valve element with a bellows chamber.
Figure 24:
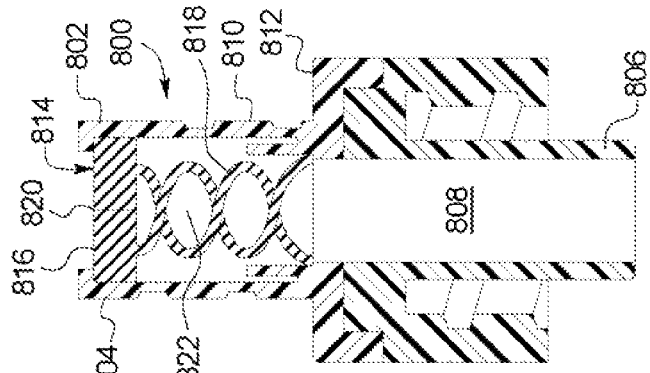
FIG. 24 is a cross-sectional view of the LAD of FIG. 23, in an open condition.

A collapsible chamber 316 extends downwardly from the upper seal 312 and communicates with the upper aperture 314. The collapsible chamber 316 includes a collapsible wall 317 and may be comprised of a thermoplastic elastomeric material and includes a normally closed low cracking (opening) pressure bi-directional seal 318 that may be provided in any of a number of configurations. In the embodiment of FIG. 7, the low pressure seal 318 is provided as a slit, opening, or hole. In the embodiments of FIGS. 21-22 and 23-24, the low pressure seal 318b comprises a cap associated with the chamber 316 to provide the slit, opening, hole, valve, or other low pressure sealing means.

Regardless of the particular configuration of the low pressure seal, it is preferably adapted to open at a lower pressure than the upper aperture 314. For example, in the embodiment of FIG. 7-8, the upper aperture 314 is adapted to open at a pressure (or back pressure) of approximately 45 PSI, while the low pressure aperture 318 is adapted to open at a pressure (or back pressure) in the range of approximately 2-6 PSI.

Preferably, a male luer 301 fully inserted into the inlet 304 will be partially received within the chamber 316, but will not extend sufficiently to penetrate the low pressure seal 318 and enter the LAD flow path 308. Accordingly, fluid communication between the LAD inlet 304 and outlet 306 requires a luer 301 inserted into the inlet 304 (to open the upper aperture 314) and fluid flow from the luer or the system associated with the outlet 306 (to open the low pressure seal 318). When fluid flow through the LAD 300 ceases, the low pressure seal 318 will automatically move to a closed condition and the luer may be removed from the inlet 304. The chamber 316 may be treated with a lubricating material to permit easy release of the luer. Alternatively, the inner surface of the chamber 316 may be roughened or textured, as in a pleated bellows (FIGS. 7-8) of wall 317 to decrease the pull force required to remove the luer. As the valve element 310 is adapted to regulate fluid flow without allowing the male luer into the LAD flow path 308, fluid displacement upon insertion and removal of the luer is substantially neutralized.

FIGS. 9-10 and 11-12 illustrate two additional LADs 400 and 400a according to the present invention. The LAD 400, 400a includes a valve housing 402, an inlet 404, an outlet 406, and a flow path 408 generally according to the foregoing description of the embodiment of FIG. 1. A valve element 410 is fixedly received within the inlet 404 to define a barrier between the flow path 408 and the outside environment. The valve element 410 comprises an upper seal 412 and a lower seal 414 spaced from each other. The upper seal 412 may be thinner than the lower seal 414 or thicker or have substantially the same thickness. It will be appreciated by those of ordinary skill in the art that the relative thicknesses of the two seals will result in varying performance characteristics, which allows the user to select a specific LAD according to his/her needs. The upper seal 412 includes a resealable upper aperture or slit 416. Referring particularly to FIGS. 9-10 the lower seal 414 includes a resealable lower aperture or slit 418. In the embodiment shown in FIGS. 11 and 12 the lower seal is formed in the configuration of a cusp valve 419. Preferably, the seals 412 and 414 and 419 are comprised of a deformable elastomeric material, such as silicone or rubber or Santoprene® elastomer. The seals 412 and 414 and 419 may be fixedly attached to the inlet 404 by any of a number of means. Suitable means include, but are not limited to, adhesive or mechanical bonding and interference overmolding.

The lower seal 414 is positioned such that a male luer fully inserted into the LAD inlet 404 will fully penetrate the aperture 416 of the upper seal 412, but only partially penetrate the aperture 418 of the lower seal 414. Preferably, the luer will contact the lower seal 414 and move the lower aperture 418 into an open condition substantially concurrently with full insertion of the luer. This may be preferred for a number of reasons. First, fluid flow through the LAD 400, 400a cannot begin until the luer is fully inserted into the inlet 404 and will cease as soon as the luer is moved away from the inlet 404. Second, by preventing the luer from protruding into the LAD flow path 408, fluid displacement during insertion and removal of the luer is substantially neutralized. Other advantages will be apparent to those of ordinary skill in the art.

FIGS. 15 and 16 illustrate a variation of the embodiments of FIGS. 9-12. The LAD 500 includes a valve housing 502, an inlet 504, an outlet 506, and a flow path 508 generally according to the foregoing description of the embodiment of FIG. 1. A valve element 510 is fixedly received within the inlet 504 to define a barrier between the flow path 508 and the outside environment. The valve element 510 comprises an upper seal 512 and a lower seal 514 spaced from each other. In contrast to the embodiments of FIGS. 8A and 8B, the lower seal 514 is configured as a split-leg opening valve that is movable between a closed condition (FIG. 15) and an open condition (FIG. 16). The upper seal 512 includes a resealable upper aperture or slit 516 and the lower seal 514 includes a resealable lower aperture or slit 518. Preferably, the valve element 510 is comprised of a deformable elastomeric material, such as silicone or rubber or Santoprene® material. The seals 512 and 514 may be molded with the apertures 516 and 518 in place, or the apertures 516 and 518 may be later added by a slitting operation.

The lower seal 514 is a deformable, unitary structure comprised of a head portion 520 and a plurality of legs 522 extending downwardly from the head portion 520. The head portion 520 is sufficiently sized to form an interference fit with the inlet 504 in the closed condition of FIG. 9A. The inlet 504 may be provided with brackets, an annular rim, or other stop means (not illustrated) adapted to receive the head portion 520 and maintain the lower seal 514 in position. In the closed condition, the legs 522 are pressed together to seal the lower aperture 518 and block fluid flow through the LAD 500. When a luer 523 is fully inserted into the inlet 504, it will contact the lower seal 514, but not enter into the LAD flow path 508. The lower seal 514 is positioned and adapted such that contact from the fully inserted male luer will impart hoop forces that deform the lower seal 514, force the legs 522 apart, and open the lower aperture 518 (FIG. 9B) to allow fluid flow through the LAD 500. Preferably, the lower seal 514 is resiliently biased to the closed condition of FIG. 9A, such that moving the luer away from the inlet 504 will automatically close the lower aperture 518. As the valve element 510 is adapted to regulate fluid flow without allowing the male luer into the LAD flow path 508, fluid displacement upon insertion and removal of the luer is substantially neutralized.

FIGS. 13-14 illustrate variations of the embodiment of FIGS. 15-16. In particular, the valve elements 510a include a generally tubular channel 524 in communication with the upper aperture 516 and the lower aperture 518. In the illustrated embodiment, a portion of the channel 524 is received by the lower aperture 518, without opening the lower aperture 518. Hence, it will be appreciated that the channel 524 provides a direct conduit between the upper and lower apertures 516 and 518. In all other respects, the valve element 510a operates substantially similarly to the embodiment of FIGS. 15 and 16 in moving the lower seal 514 from a closed condition (FIG. 13) to an open condition (FIG. 14).

FIGS. 17 and 18 illustrate a LAD 600 having a valve housing 602, an inlet 604, an outlet 606, and a flow path 608 generally according to the foregoing description of the embodiment of FIG. 1. A valve element 610 is comprised of an upper seal 612 and a lower seal 614 fixedly attached to the inlet 604. The upper seal 612 is preferably a septum-like member having an upper resealable aperture or slit 616 adapted to receive a male luer 617 inserted into the inlet 604. The upper seal 612 is substantially comprised of a deformable elastomeric material, such as silicone or rubber or Santoprene® elastomer.

The lower seal 614 can be understood as a generally tubular member with cup-shaped portions removed from its upper and lower ends to define an upper void volume 618 and a lower void volume 620. The volumes 618 and 620 are separated by a lower resealable aperture 622 that is movable between a closed condition (FIG. 17) and an open condition (FIG. 18). Preferably, the lower seal 614 is comprised of a compressible, deformable material. When used herein, the term "compressible" refers to a material that is capable of decreasing in volume by more than a nominal amount upon insertion of a male luer into the inlet 604. For example, a silicone or elastomeric material is deformable, because it will change shape to accommodate a male luer, but it is not compressible because it is not capable of a substantial reduction in volume. Those of ordinary skill in the art will appreciate that, when using known elastomeric slit septa, the open internal volume of the valve (i.e., the portion of the valve interior that is available for fluid flow) will substantially decrease upon insertion of a male luer, because the valve interior must receive the combined volumes of the male luer and the deformed valve element, instead of just the volume of the valve element. This change in open internal volume may impart a positive displacement of fluid through the outlet during the insertion of the male luer, which may be undesirable in certain applications. Hence, through the use of a compressible lower seal 614, the change in available flow path volume may be reduced or minimized to limit or avoid the effects of positive fluid displacement.

Preferably, the lower seal 614 is substantially comprised of a compressible polymeric foam with a closed-cell structure, such as a silicone or urethane foam. A closed-cell structure is typically more rigid and less compressible than an open-cell structure, so such a configuration may be preferred for ensuring a tight seal immediately before a male luer is fully inserted into the inlet 604 and immediately after the luer is removed therefrom. The lower seal 614 is preferably harder than the upper seal 612 (~70-80 D vs. ~40-50 D in one embodiment) to provide a relatively high pressure seal. The foam may also be treated with a lubricant or anti-microbial gel or liquid or any other performance-enhancing material.

In use, a male luer 617 is inserted into the inlet 604 and penetrates the upper aperture 616, thereby deforming the upper seal 612 and moving it partially into the upper void volume 618. The luer is further inserted into the inlet 604 and contacts the lower seal 614. Preferably, the lower seal 614 is positioned such that a fully inserted luer will enter into the lower aperture 622 without moving beyond the aperture 622 and entering the lower void volume 620 or LAD flow path 608. A luer so inserted will compress the lower seal 614 outwardly against the wall of the inlet 604 and open the lower aperture 622 to allow fluid flow through the LAD 600. As the valve element 610 is adapted to regulate fluid flow without allowing the male luer into the LAD flow path 608 or lower void volume 620, fluid displacement upon insertion and removal of the luer is substantially neutralized. The incidence of fluid displacement is even further minimized by the use of a compressible lower seal 614 that compresses outwardly, rather than deforming downwardly, as described previously herein.

FIGS. 19 and 20 illustrate yet another embodiment of a LAD according to the present invention, generally designated as 700. The LAD 700 includes a valve housing 702, an inlet 704, an outlet 706, and a flow path 708 generally according to the foregoing description of the embodiment of FIG. 1. A valve element 710 is fixedly received within the inlet 704 to define a barrier between the flow path 708 and the outside environment. The valve element 710 comprises a deformable upper seal or septum 712 defining a resealable upper aperture or slit 714 therethrough. The upper seal 712 is fixedly mounted to normally block and seal the inlet 704. A barbed void volume arrow 716 extends downwardly from the upper seal 712 and communicates with the upper aperture 714. The barbed void volume arrow 716 includes a tapered portion 718 defining a lower aperture 720 that is movable between a closed condition (FIG. 19) and an open condition (FIG. 20). The external surface of the tapered portion 718 includes a plurality of radially projecting barbs 722 spaced from the wall of the inlet 704 in the closed condition and adapted to contact the wall when the lower aperture 720 is in the open condition. The barbs 722 may be provided as generally annular members to establish a circumferential seal between the tapered portion 718 and the inlet 704 in the condition of FIG. 20. This may be preferred to avoid the creation of a fluid stagnation region between the barbed void volume arrow 716 and the inlet 704 during fluid flow through the LAD 700.

Preferably, the valve element 710 is provided as a unitary piece, comprised of a deformable elastomeric material, such as silicone or rubber or Santoprene®. The upper seal 712 may be fixedly attached to the inlet 704 by any of a number of means. Suitable means include, but are not limited to, adhesive or mechanical bonding and interference overmolding.

In use, a male luer 723 is inserted into the inlet 704 and deforms the upper seal 712 to penetrate through the upper aperture 714. The male luer is further inserted into the inlet 704 to deform the barbed void volume arrow 716, thereby moving the barbs 722 against the housing 702 and opening the lower aperture 720. An additional benefit of the barbs 722 is realized during insertion of the luer into the inlet 704. As described previously herein, it may be preferred to cause the tapered portion 718 to contact the housing 702 and create a fluid seal. In comparison to a tapered portion 718 having a substantially smooth outer surface, a tapered portion 718 having a plurality of barbs 722 will minimize the compressive force generated when the lower aperture 720 opens and the barbed void volume arrow 716 is pressed against the inlet 704. Preferably, the valve element 710 is adapted such that a fully inserted luer will open the lower aperture 720 without extending into the flow path 708.

When fluid flow through the LAD 700 is completed, the luer is moved away from the inlet 704. Preferably, the tapered portion 718 is resiliently biased to the closed condition so that it will automatically close the lower aperture 720 when the luer is removed. By regulating fluid flow through the LAD 700 without requiring the luer to enter the LAD flow path 708, fluid displacement during insertion and removal of the luer is substantially neutralized.

Figure 25:
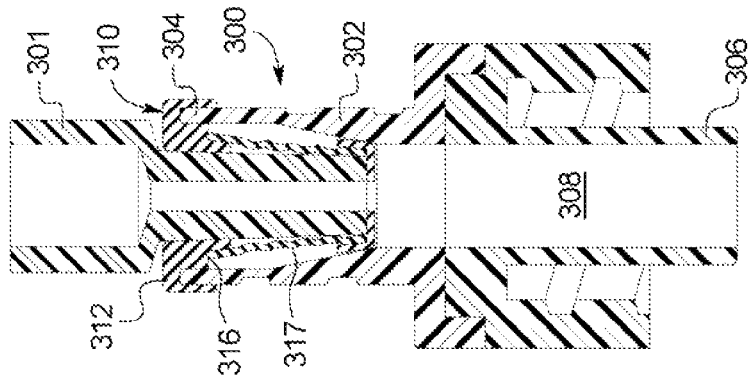
FIG. 25 is a cross-sectional view of a LAD having a torque-activated valve element.
Figure 26:
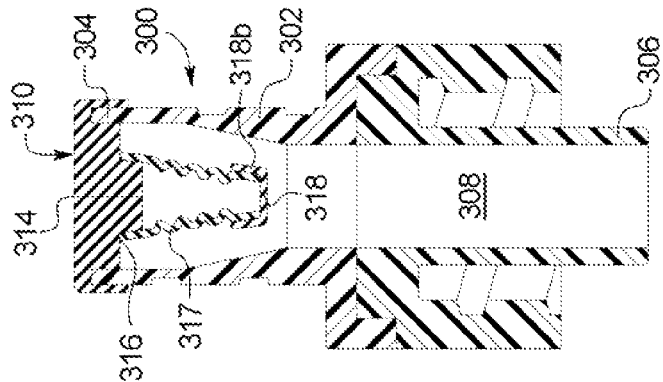
FIG. 26 is a cross-sectional view of the LAD of FIG. 25, in an open condition.

The LAD 800 of FIGS. 25 and 26 includes a valve housing 802, an inlet 804, an outlet 806, and a flow path 808 generally according to the foregoing description of the embodiment of FIG. 1. An upper housing portion 810 is rotatably associated with a lower housing portion 812, such that the upper and lower housing portions may be rotated with respect to each other. This connection may be accomplished by any of a number of means, such as by way of an aligned rib and groove mechanism.

A valve element 814 is received within the inlet 804 and comprises an upper seal or septum 816 and a torque-activated valve 818 extending downwardly from the upper seal 816. The upper seal 816 is fixedly attached to the upper housing portion 810 and a lower section of the torque-activated valve 818 is fixedly attached to the lower housing portion 812. Hence, it will be appreciated that rotation of the upper housing portion 810 with respect to the lower housing portion 812 will impart torsion forces to the torque-activated valve 818.

The upper seal 816 defines a resealable aperture 820 in communication with a resealable lumen 822 of the torque-activated valve 818. The torque-activated valve 818 is preferably biased to a closed condition, wherein the lumen 822 is initially closed prior to rotation of the housing portions 810 and 812. When the housing portions 810 and 812 are rotated with respect to each other, the upper end of the torque-activated valve 818 is twisted with respect to the lower end to create a torsion force that opens the lumen 822. The lumen 822 remains open until the upper and lower housing portions 810 and 812 are returned to their original position relative to each other.

In contrast to the lumen 822 of the torque-activated valve 818, the aperture 820 of the upper seal 816 is not opened by rotation of the housing portions 810 and 812, but by insertion of a male luer 821 Accordingly, fluid flow through the LAD 800 cannot be achieved until a luer is inserted into the inlet 804 and the housing portions 810 and 812 are rotated with respect to each other.

A common system for locking a luer onto an LAD is to use mating threads, as described herein with respect to the embodiment of FIG. 1. Preferably, the valve element 814 is adapted to open as the luer is locked onto the inlet 804. In particular, a luer inserted into the inlet 804 will deform the upper seal 816 and penetrate through the aperture 820 to open the same. The lower housing portion 812 is gripped and a threaded collar of the luer (not illustrated) is rotated to mate with external threads 825 of the inlet 804). The upper housing portion 810 will tend to rotate as the luer is locked to the inlet 804, especially after the luer threads have been securely mated with the inlet threads, and the lumen 822 of the torque-activated valve 818 will be twisted and opened by the same motion. An unlocking rotation of the luer will have the opposite effect, thereby closing the lumen 822 and flow through the LAD 800 prior to removal of the luer from the inlet 804. It will be appreciated that the valve element 814 regulates flow through the LAD 800 without requiring the luer to enter the LAD flow path 808, so fluid displacement during insertion and removal of the luer is substantially neutralized.

FIGS. 27 and 28 illustrate still another embodiment of a LAD 900 according to the present invention. The LAD 900 includes a valve housing 902, an inlet 904, an outlet 906, and a flow path 908 generally according to the foregoing description of the embodiment of FIG. 1. In one embodiment, the housing 902 comprises an upper housing portion 910 secured to a lower housing portion 912. An upper end of the outlet 906 extends upwardly into the upper housing portion 910 to define a generally tubular stand pipe 914, which will be described in greater detail herein.

A valve element 916 is received within the inlet 904 to define a barrier between the flow path 908 and the outside environment. The valve element 916 comprises an upper seal 918 and a resealable over sleeve 920 surrounding the stand pipe 914. The upper seal 918 and over sleeve 920 are deformable, and preferably comprised of an elastomeric material, such as silicone or rubber or Santoprene® material.

The upper seal 918 defines a resealable upper aperture or slit 922 adapted to receive a male luer (not illustrated) and is preferably mechanically fixed within the upper housing portion 910.

The over sleeve 920 defines a lower aperture 924 and is movable between a closed condition (FIG. 27) and an open condition (FIG. 28). In the closed condition, the over sleeve 920 covers and blocks flow through the stand pipe 914. When a male luer 925 is inserted into the inlet 904, it penetrates through the upper aperture 922 and contacts the over sleeve 920. A fully inserted luer will push the over sleeve 920 down and around the stand pipe 914, thereby opening the lower aperture 924 and exposing the stand pipe 914 to allow flow through the LAD 900. When the luer is moved away from the inlet 904, the over sleeve 920 will resiliently return to the closed condition of FIG. 27, which closes the lower aperture 924 and prevents flow through the LAD 900. Hence, it will be seen that the valve element 916 regulates flow through the LAD 900 without allowing the luer to enter the LAD flow path 908, so fluid displacement upon insertion and removal of the luer is substantially neutralized.

FIGS. 31 and 32 illustrate another embodiment of a LAD 1000 according to the present invention. The LAD 1000 includes a valve housing 1002, an inlet 1004, an outlet 1006, and a flow path 1008 generally according to the foregoing description of the embodiment of FIG. 1. A valve element 1010 is fixedly received within the inlet 1004 to define a barrier between the flow path 1008 and the outside environment. The valve element 1010 comprises an upper seal 1012 with a plurality of flexible sealing arms or flanges 1014 extending away from a bottom surface of the upper seal 1012. Preferably, the valve element 1010 is a unitary structure comprised of a deformable elastomeric material, such as silicone or rubber or Santoprene® elastomer.

The upper seal 1012 defines a resealable upper aperture or slit 1016 adapted to receive a male luer (not illustrated) and the sealing flanges 1014 meet at a point to define a resealable lower aperture 1018 movable between a closed condition (FIG. 31) and an open condition (FIG. 32). The sealing flanges 1014 may be substantially identical to each other or may have opposing thick and thin wall sections (not illustrated) having differing deformation properties, which may aid in opening and/or closing the lower aperture 1018.

The sealing flanges 1014 may have a generally "dogleg" configuration to define an open chamber 1020 in communication with the upper and lower apertures 1016 and 1018. In the closed condition of FIG. 31, the chamber 1020 is sealed off from the atmosphere (by the closed upper aperture 1016) and the LAD flow path 1008 (by the closed lower aperture 1018). Referring to FIG. 31, the upper aperture 1018 is opened by inserting a male luer 1025 into the inlet 1004 and deforming the upper seal 1012. The lower aperture 1018 will move to an open condition (FIG. 32) when the luer 1025 is fully inserted into the inlet 1004. This may be achieved by at least two different means. First, the sealing flanges 1014 may be adapted to deform upon contact with a luer and to spread apart and open the lower aperture 1016 when the luer 1025 has been fully inserted. Alternatively, the sealing flanges 1014 may be relatively thin, such that they provide a low pressure seal at the lower aperture 1016 that is adapted to open upon fluid flow from the luer or from the system associated with the LAD outlet 1006.

Regardless of the nature of the lower aperture 1016, the valve element 1010 is preferably adapted such that a fully inserted luer will enter into the chamber 1020, but not the LAD flow path 1008. By confining the luer to the chamber 1020, it will not alter the open volume of the LAD flow path 1008, so fluid displacement upon insertion and removal of the luer is substantially neutralized.

FIGS. 33 and 34 illustrate yet another embodiment of a LAD according to the present invention, generally designated as 1100. The LAD 1100 includes a valve housing 1102, an inlet 1104, an outlet 1106, and a flow path 1108 generally according to the foregoing description of the embodiment of FIG. 1. A valve element 1110 is received within the inlet 1104 to define a barrier between the flow path 1108 and the outside environment. The valve element 1110 comprises a deformable upper seal or septum 1112 defining a resealable first aperture or slit 1114 therethrough. The upper seal 1112 is comprised of an elastomeric material and fixedly mounted to normally block and seal the inlet 1104. Preferably, the upper seal 1112 is comprised of a deformable elastomeric material, such as silicone or rubber or Santoprene® material and is fixedly attached to the inlet 1104 by any of a number of means. Suitable means include, but are not limited to, adhesive or mechanical bonding and interference overmolding.

A cammed seal cap 1116 is secured to a lower surface of the upper seal 1112 and extends downwardly therefrom. The seal cap 1116 is preferably comprised of a thermoplastic material and defines a lower aperture 1118 movable between a closed condition (FIG. 33) and an open condition (FIG. 34). The seal cap 1116 includes one or more inwardly projecting cam surfaces 1120. The cam surfaces 1120 have an inner diameter less than the outer diameter of a male luer 1125 adapted to be inserted into the LAD inlet 1104, such that a luer so inserted will penetrate through the upper aperture 1114 and bear against the cam surfaces 1120. The cam surfaces 1120 are pressed outwardly by the luer, which causes the seal cap 1116 to deform and opens the lower aperture 1118 to allow fluid flow through the LAD 1100. Preferably, the valve element 1110 is adapted such that a fully inserted luer 1125 will open the lower aperture 1118 without penetrating the lower aperture 1118 and entering the LAD flow path 1108. As the valve element 1110 is adapted to regulate fluid flow without allowing the male luer into the LAD flow path 1108, fluid displacement upon insertion and removal of the luer is substantially neutralized.

While the present invention has been described in terms of certain preferred and alternative embodiments for purposes of illustration, it is not limited to the precise embodiments shown or to the particular features, shapes or sizes illustrated. A variety of changes may be made without departing from the present invention as defined by the appended claims.

The invention claimed is:

1. A medical valve for the bi-directional transfer of fluid, comprising:
   a valve housing having an inlet adapted to receive a male luer, an outlet, and a flow path defined therebetween; and
   a valve element closing the inlet of the valve housing, said valve element including a first and second normally closed resealable apertures, the first aperture having a higher opening pressure than the second aperture, the first and second apertures surrounding a space adapted to receive a male luer to allow fluid to be transferred between the male luer and the flow path, wherein there is substantially no fluid displacement when at least a portion of the male luer is inserted into or removed from the space, and wherein the second aperture is opened via pressure from a fluid introduced at the fluid outlet.

2. The medical valve of claim 1, which includes a septum closing the inlet of the valve housing, the septum defining the first aperture, and a seal spaced apart from the septum, the seal defining the second aperture.

3. The medical valve of claim 2, wherein the seal is spaced apart from the septum by a collapsible wall.

4. The medical valve of claim 2, wherein the seal is a cap fitted to a wall extending from the septum.

5. The medical valve of claim 2, wherein the seal is spaced apart from the septum such that the seal is unpenetrated by the male when fully inserted into the valve housing.

6. The medical valve of claim 1, wherein the higher opening pressure is multiple times greater than the lower opening pressure.

7. The medical valve of claim 1, wherein the second aperture closes automatically upon completion of fluid transfer through the medical valve.

8. The medical valve of claim 7, the valve element configured to ease removal of the male luer after automatic closing of the second aperture.

9. The medical valve of claim 8, wherein the valve element is lubricated to ease male luer removal.

10. The medical valve of claim 8, wherein the valve element is textured to ease male luer removal.

11. A medical fluid valve for the bi-directional transfer of fluid, comprising:
    a valve housing having an inlet adapted to receive a male luer, an outlet, and a flow path defined therebetween; and
    a valve element including (i) a septum sealing the inlet, the septum defining a first aperture, (ii) a seal defining a second aperture, and (iii) a chamber wall separating the seal from the septum, the chamber wall constructed and arranged such that the male luer when fully received within the valve housing opens only the first aperture.

12. The medical fluid valve of claim 11, wherein the chamber wall is collapsible to allow the wall to expand and unfold upon insertion of the male luer.

13. The medical fluid valve of claim 11, wherein the chamber wall is stretchable to allow the male luer when fully received within the valve housing to open only the first aperture.

14. The medical fluid valve of claim 11, wherein the chamber wall is elongated such that the male luer when fully received within the valve housing opens only the first aperture.

15. The medical fluid valve of claim 11, wherein seal is radially sized to receive the entire tip of the male luer.

16. The medical fluid volume of claim 11, wherein the seal is configured to allow the second aperture to be opened via pressure of fluid introduced at the valve housing outlet.

17. A medical fluid valve for the bi-directional transfer of fluid, comprising:
a valve housing having an inlet adapted to receive a male luer, an outlet, and a flow path defined therebetween; and
a valve element including (i) a septum sealing the inlet, the septum defining a first aperture, (ii) a seal defining a second aperture, and (iii) a chamber wall separating the seal from the septum, the chamber wall constructed and arranged to allow the seal to be contacted by the male luer when fully inserted without piercing the seal.

18. The medical fluid valve of claim 17, wherein the septum, seal and chamber wall define a male luer receiving space that allows fluid to be transferred between the male luer and the flow path, and which at least substantially prevents fluid displacement when the male luer is inserted into or removed from the space.

19. The medical fluid valve of claim 18, wherein the seal is configured to allow the second aperture to be opened via pressure of fluid residing within the flow path.

20. A medical valve for the bi-directional transfer of fluid, comprising:
a valve housing having an inlet adapted to receive a male luer, an outlet, and a flow path defined therebetween; and
a valve element closing the inlet of the valve housing, said valve element including a first and second normally closed resealable apertures, the first aperture having a higher opening pressure than the second aperture, the first and second apertures surrounding a space adapted to receive a male luer to allow fluid to be transferred between the male luer and the flow path, wherein there is substantially no fluid displacement when at least a portion of the male luer is inserted into or removed from the space, and wherein the second aperture closes automatically upon completion of fluid transfer through the medical valve.

21. A medical valve for the bi-directional transfer of fluid, comprising:
a valve housing having an inlet adapted to receive a male luer, an outlet, and a flow path defined;
a valve element closing the inlet of the valve housing, said valve element including a first and second normally closed resealable apertures, the first aperture having a higher opening pressure than the second aperture, the first and second apertures surrounding a space adapted to receive a male luer to allow fluid to be transferred between the male luer and the flow path, wherein there is substantially no fluid displacement when at least a portion of the male luer is inserted into or removed from the space; and
which includes a septum closing the inlet of the valve housing, the septum defining the first aperture, and a seal spaced apart from the septum, the seal defining the second aperture, and wherein the seal is spaced apart from the septum by a collapsible wall.

* * * * *